United States Patent
Lazarus

(10) Patent No.: US 10,232,150 B2
(45) Date of Patent: Mar. 19, 2019

(54) BODY CAVITY DRAINAGE DEVICES AND RELATED METHODS

(71) Applicant: Merit Medical Systems, Inc., West Jordan, UT (US)

(72) Inventor: Harrison M. Lazarus, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 352 days.

(21) Appl. No.: 13/840,986

(22) Filed: Mar. 15, 2013

(65) Prior Publication Data

US 2013/0211385 A1    Aug. 15, 2013

Related U.S. Application Data

(63) Continuation-in-part of application No. 13/045,274, filed on Mar. 10, 2011, now abandoned.

(Continued)

(51) Int. Cl.
*A61M 1/00* (2006.01)
*A61M 27/00* (2006.01)
(Continued)

(52) U.S. Cl.
CPC ............ *A61M 27/00* (2013.01); *A61M 1/008* (2013.01); *A61M 25/003* (2013.01);
(Continued)

(58) Field of Classification Search
CPC ...... A61F 27/00; A61F 25/0147; A61F 1/008; A61M 27/00; A61M 25/0147;
(Continued)

(56) References Cited

U.S. PATENT DOCUMENTS 2,393,002 A    1/1946  Smith
2,898,917 A    8/1959  Wallace
(Continued)

FOREIGN PATENT DOCUMENTS

RU    2012371 C1    5/1994
RU    2415682 C1    4/2011
(Continued)

OTHER PUBLICATIONS

Ben-Isaac et al., "Flexible Fiberoptic Pleuroscopy: Pleural and Lung Biopsy*," Experimental Approaches, Chest Journal No. 67, <http://journal.publications.chestnet.org/data/Journals/CHEST/20966/573.pdf>, May 5, 1975, pp. 573-576.

(Continued)

*Primary Examiner* — Andrew J Mensh
(74) *Attorney, Agent, or Firm* — Stoel Rives LLP

(57) ABSTRACT

Body cavity drainage devices and associated methods are disclosed herein. In some embodiments a body cavity drainage device comprises a drainage tube having a proximal end and a distal end; and an automated means to move the distal end of the drainage tube about a body cavity of a patient. In some embodiments, the distal end of the drainage tube may be moved by one or more of the application of a magnetic field, the insertion or withdrawal of fluid from a closed lumen, and manipulation by an external motion generator. In additional embodiments, a body cavity drainage device includes at least a second open lumen for the insertion of a fluid into a body cavity. In yet further embodiments, an internal tissue may be massaged from within a body cavity of a patient.

20 Claims, 14 Drawing Sheets

Related U.S. Application Data

(60) Provisional application No. 61/312,878, filed on Mar. 11, 2010.

(51) Int. Cl.
*A61M 25/00* (2006.01)
*A61M 25/01* (2006.01)

(52) U.S. Cl.
CPC .... *A61M 25/0054* (2013.01); *A61M 25/0127* (2013.01); *A61M 25/0136* (2013.01); *A61M 25/007* (2013.01); *A61M 25/0041* (2013.01); *A61M 25/0147* (2013.01); *A61M 25/0155* (2013.01); *A61M 2025/004* (2013.01); *A61M 2025/0037* (2013.01); *A61M 2025/0063* (2013.01); *A61M 2025/015* (2013.01); *A61M 2210/101* (2013.01)

(58) Field of Classification Search
CPC .............. A61M 1/008; A61M 25/003; A61M 25/0155; A61M 25/0127; A61M 25/0136; A61M 25/0041; A61M 25/007; A61M 2025/0037; A61M 2025/004; A61M 2025/0063; A61M 2025/015; A61M 2210/101
USPC ......................................................... 604/540
See application file for complete search history.

(56) References Cited

U.S. PATENT DOCUMENTS

| | | |
|---|---|---|
| 3,225,762 A | 12/1965 | Guttman |
| 3,416,532 A | 12/1968 | Grossman |
| 3,610,231 A | 10/1971 | Takahashi et al. |
| 3,683,929 A | 8/1972 | Holter |
| 3,830,238 A | 8/1974 | Kurtz et al. |
| 3,863,641 A | 2/1975 | Popa |
| 3,867,945 A | 2/1975 | Long |
| 3,937,418 A | 2/1976 | Critelli |
| 3,943,929 A | 3/1976 | Patel |
| 4,068,383 A | 1/1978 | Krebs |
| 4,105,031 A | 8/1978 | Kurtz et al. |
| 4,202,510 A | 5/1980 | Stanish |
| 4,203,430 A | 5/1980 | Takahashi |
| 4,228,802 A | 10/1980 | Trott et al. |
| 4,439,189 A | 3/1984 | Sargeant et al. |
| 4,571,239 A | 2/1986 | Heyman |
| 4,580,551 A | 4/1986 | Siegmund et al. |
| 4,608,982 A | 9/1986 | Pollard |
| 4,692,154 A | 9/1987 | Singery et al. |
| 4,769,019 A | 9/1988 | Kerwin |
| 4,862,891 A | 9/1989 | Smith |
| 4,883,474 A | 11/1989 | Sheridan et al. |
| 4,920,980 A | 5/1990 | Jackowski |
| 5,026,358 A | 6/1991 | Everett et al. |
| 5,040,543 A | 8/1991 | Badera et al. |
| 5,047,018 A | 9/1991 | Gay et al. |
| 5,108,368 A | 4/1992 | Hammerslag et al. |
| 5,141,503 A | 8/1992 | Sewell |
| 5,157,813 A | 10/1992 | Carroll |
| 5,205,830 A | 4/1993 | Dassa et al. |
| 5,207,661 A | 5/1993 | Repschlager |
| 5,211,644 A | 5/1993 | Vanbeek et al. |
| 5,297,310 A | 3/1994 | Cox et al. |
| 5,300,050 A | 4/1994 | Everett et al. |
| 5,312,357 A | 5/1994 | Buijs et al. |
| 5,364,351 A | 11/1994 | Heinzelman et al. |
| 5,370,610 A | 12/1994 | Reynolds et al. |
| 5,397,321 A | 3/1995 | Houser et al. |
| 5,409,462 A | 4/1995 | Ross |
| 5,409,468 A | 4/1995 | Sachse |
| 5,456,664 A | 10/1995 | Heinzelman et al. |
| 5,540,648 A | 7/1996 | Yoon et al. |
| 5,601,087 A | 2/1997 | Gunderson et al. |
| 5,616,131 A | 4/1997 | Sauer et al. |
| 5,630,795 A * | 5/1997 | Kuramoto ......... A61B 1/00068 600/153 |
| 5,653,696 A | 8/1997 | Shiber et al. |
| 5,772,670 A | 6/1998 | Brosa |
| 5,807,341 A | 9/1998 | Heim |
| 5,895,400 A * | 4/1999 | Abela ............... 606/159 |
| 5,897,534 A | 4/1999 | Heim et al. |
| 5,987,344 A | 11/1999 | West et al. |
| 6,045,623 A | 4/2000 | Cannon et al. |
| 6,146,355 A | 11/2000 | Biggs |
| 6,171,277 B1 | 1/2001 | Ponzi |
| 6,183,450 B1 | 2/2001 | Lois |
| 6,193,691 B1 | 2/2001 | Beardsley |
| 6,254,581 B1 | 7/2001 | Scott |
| 6,468,260 B1 | 10/2002 | Bumbalough et al. |
| 6,500,167 B1 | 12/2002 | Webster |
| 6,514,273 B1 | 2/2003 | Voss et al. |
| 6,530,913 B1 | 3/2003 | Giba et al. |
| 6,530,935 B2 | 3/2003 | Wensel et al. |
| 6,638,253 B2 | 10/2003 | Breznock |
| 6,907,992 B2 | 6/2005 | McMichael et al. |
| 7,037,290 B2 | 5/2006 | Gardeski et al. |
| 7,407,128 B1 | 8/2008 | Chang |
| 7,497,854 B2 * | 3/2009 | Gill et al. .............. 604/544 |
| 7,578,814 B2 * | 8/2009 | Accisano, III ...... A61M 25/007 600/585 |
| 7,740,623 B2 | 6/2010 | Nayak et al. |
| 7,758,586 B2 | 7/2010 | Muto et al. |
| 8,220,460 B2 | 7/2012 | Tanaka |
| 8,246,752 B2 | 8/2012 | Boyle, Jr. |
| D669,168 S | 10/2012 | Krueger et al. |
| D669,577 S | 10/2012 | Holsinger |
| 8,388,759 B2 | 3/2013 | Boyle, Jr. et al. |
| 8,409,070 B2 | 4/2013 | Carol et al. |
| D700,322 S | 2/2014 | Kleiner |
| D708,741 S | 7/2014 | Harrison et al. |
| D710,495 S | 8/2014 | Wu et al. |
| 8,870,892 B2 | 10/2014 | Feng et al. |
| D718,440 S | 11/2014 | Besse et al. |
| D724,725 S | 3/2015 | Chang |
| 8,979,744 B2 | 3/2015 | Braga et al. |
| D726,304 S | 4/2015 | Yatabe et al. |
| D728,781 S | 5/2015 | Pierson et al. |
| D732,160 S | 6/2015 | Du |
| 9,604,033 B2 | 3/2017 | Lazarus |
| 9,649,415 B2 | 5/2017 | Lazarus |
| 9,821,097 B2 | 11/2017 | Lazarus |
| 2001/0005785 A1 | 6/2001 | Sachse |
| 2001/0007922 A1 | 7/2001 | Schwager |
| 2003/0208252 A1* | 11/2003 | O' Boyle ........... A61B 18/1492 607/122 |
| 2003/0225364 A1* | 12/2003 | Kraft ................... A61B 10/025 604/35 |
| 2003/0236493 A1 | 12/2003 | Mauch |
| 2004/0035017 A1 | 2/2004 | Yang |
| 2004/0059293 A1* | 3/2004 | Chu ................... A61J 15/0015 604/107 |
| 2004/0116852 A1 | 6/2004 | Scopton |
| 2004/0143197 A1 | 7/2004 | Soukup et al. |
| 2005/0131393 A1 | 6/2005 | Chu |
| 2005/0184186 A1 | 8/2005 | Tsoi et al. |
| 2005/0277875 A1 | 12/2005 | Selkee |
| 2006/0069311 A1 | 3/2006 | Sullivan |
| 2006/0142695 A1* | 6/2006 | Knudson ................ 604/95.04 |
| 2006/0173449 A1 | 8/2006 | Sharareh et al. |
| 2006/0217667 A1 | 9/2006 | Accisano et al. |
| 2006/0264925 A1 | 11/2006 | Sharareh et al. |
| 2006/0264988 A1 | 11/2006 | Boyle |
| 2006/0280773 A1 | 12/2006 | Roschak et al. |
| 2007/0016133 A1 | 1/2007 | Pepper |
| 2007/0060997 A1 | 3/2007 | de Boer |
| 2007/0078455 A1* | 4/2007 | Rashidi ............. A61B 18/1492 606/41 |
| 2007/0156116 A1 | 7/2007 | Gonzalez |
| 2007/0167923 A1 | 7/2007 | Deal |
| 2007/0287993 A1 | 12/2007 | Hinman et al. |
| 2008/0021415 A1 | 1/2008 | Durkin et al. |
| 2008/0045921 A1 | 2/2008 | Anderson et al. |

(56) References Cited

U.S. PATENT DOCUMENTS

| | | |
|---|---|---|
| 2008/0097293 A1 | 4/2008 | Chin et al. |
| 2008/0125848 A1 | 5/2008 | Kusleika et al. |
| 2008/0214948 A1 | 9/2008 | Myklebust et al. |
| 2008/0236209 A1 | 10/2008 | Conti et al. |
| 2008/0249483 A1* | 10/2008 | Slenker ............... A61B 1/0055 604/275 |
| 2008/0300462 A1* | 12/2008 | Intoccia ............. A61B 1/00071 600/146 |
| 2009/0005771 A1 | 1/2009 | Lieber et al. |
| 2009/0012365 A1 | 1/2009 | Ueno et al. |
| 2009/0062769 A1 | 3/2009 | Graves et al. |
| 2009/0227900 A1 | 9/2009 | Kim et al. |
| 2009/0270800 A1 | 10/2009 | Spurchise et al. |
| 2009/0270838 A1 | 10/2009 | Berthiaume et al. |
| 2009/0299327 A1 | 12/2009 | Tilson et al. |
| 2010/0070024 A1 | 3/2010 | Venturelli et al. |
| 2010/0101061 A1 | 4/2010 | Ha |
| 2010/0137775 A1 | 6/2010 | Hu et al. |
| 2010/0145368 A1 | 6/2010 | Chu et al. |
| 2010/0168731 A1 | 7/2010 | Wu et al. |
| 2010/0191057 A1 | 7/2010 | Jansen et al. |
| 2010/0222664 A1 | 9/2010 | Lemon et al. |
| 2010/0234799 A1 | 9/2010 | Paris et al. |
| 2010/0249490 A1 | 9/2010 | Farnan |
| 2010/0249520 A1 | 9/2010 | Shelton, IV et al. |
| 2010/0264244 A1 | 10/2010 | Spencer |
| 2011/0040285 A1 | 2/2011 | Boyle |
| 2011/0062268 A1 | 3/2011 | Cheng |
| 2011/0077498 A1 | 3/2011 | McDaniel |
| 2011/0197888 A1 | 8/2011 | Deutsch et al. |
| 2011/0213300 A1 | 9/2011 | McWeeney et al. |
| 2011/0224647 A1 | 9/2011 | Lazarus |
| 2011/0264089 A1 | 10/2011 | Zirkle et al. |
| 2011/0282153 A1 | 11/2011 | Ueki |
| 2012/0116161 A1 | 5/2012 | Nieman et al. |
| 2012/0157921 A1 | 6/2012 | Hoofnagle et al. |
| 2012/0172703 A1 | 7/2012 | Esguerra et al. |
| 2013/0023840 A1 | 1/2013 | Loske et al. |
| 2013/0046250 A1 | 2/2013 | Bode |
| 2013/0158379 A1 | 6/2013 | Selkee |
| 2013/0184642 A1 | 7/2013 | O'Donnell et al. |
| 2013/0204087 A1 | 8/2013 | Jaworek et al. |
| 2013/0211385 A1 | 8/2013 | Lazarus |
| 2013/0253505 A1 | 9/2013 | Schultz |
| 2013/0276718 A1 | 10/2013 | Valadez et al. |
| 2013/0310767 A1 | 11/2013 | Solar et al. |
| 2014/0150782 A1 | 6/2014 | Vazales et al. |
| 2014/0193138 A1 | 7/2014 | Koren |
| 2014/0290014 A1 | 10/2014 | Myrick |
| 2015/0148595 A1 | 5/2015 | Bagwell et al. |
| 2015/0157399 A1 | 6/2015 | Romoscanu |
| 2015/0374889 A1 | 12/2015 | Lazarus |
| 2015/0374959 A1 | 12/2015 | Lazarus |
| 2017/0050041 A1 | 2/2017 | Cosman |
| 2017/0143940 A1 | 5/2017 | Flygare et al. |

FOREIGN PATENT DOCUMENTS

| | | |
|---|---|---|
| WO | 9325264 A1 | 12/1993 |
| WO | 9952481 A1 | 10/1999 |

OTHER PUBLICATIONS

"Catheter prevents clogging," Research & Development, <<http://www.rdmag.com/printpdf/award-winners/2011/08/catheter-prevents-clogging>>, Aug. 14, 2011, 3 pages.

"Medical pleuroscopy", <http://www.cancercenter.com/treatments/medical-pleuroscopy/>, Cancer Treatment Centers of America, retrieved Aug. 19, 2013, 2 Pages.

"Rocket® Cardiothoracic Range," Rocketmedical, Issue 1, R89947, Jan. 2011, 23 pages.

"Express Dry Seal Chest Drain, Instructions for Use," Atrium, www.atriummed.com (2003) 2 pages.

Office Action dated Sep. 12, 2017 for U.S. Appl. No. 14/318,571.

International Preliminary Report and Written Opinion dated Dec. 27, 2016 for PCT/US2015/038112.

International Search Report and Written Opinion dated Aug. 27, 2015 for PCT/US2015/038086.

International Search Report and Written Opinion dated Oct. 1, 2015 for PCT/US2015/038112.

International Search Report dated Sep. 3, 2015 for PCT/US2015/038102.

Office Action dated May 11, 2017 for U.S. Appl. No. 14/318,571.

International Search Report and Written Opinion dated Mar. 8, 2017 for PCT/US2016/063251.

'Occlutech Steerable Guiding Sheath, 2015.

* cited by examiner

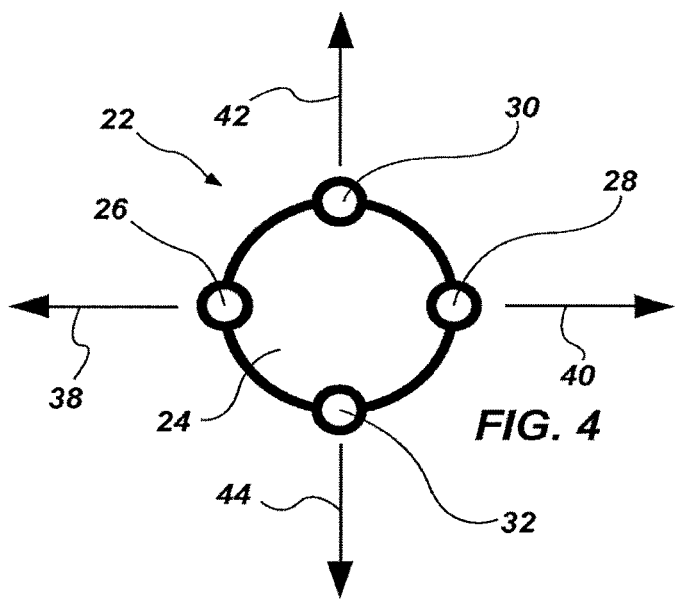
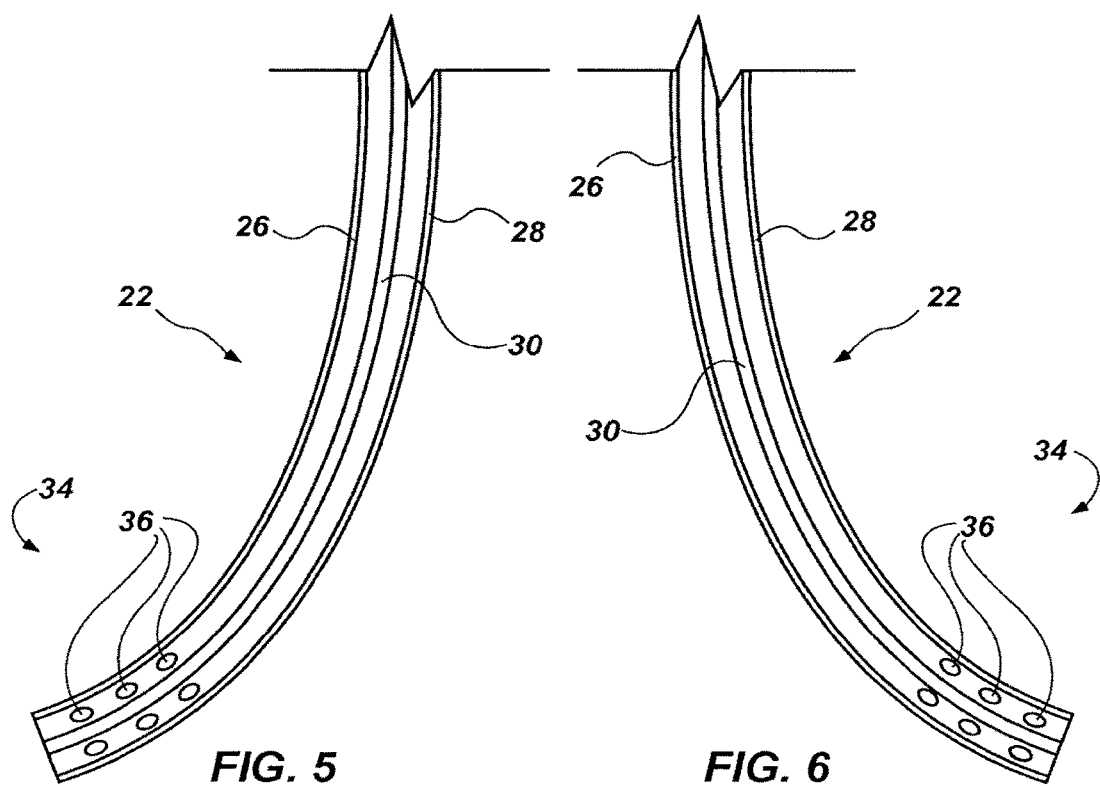

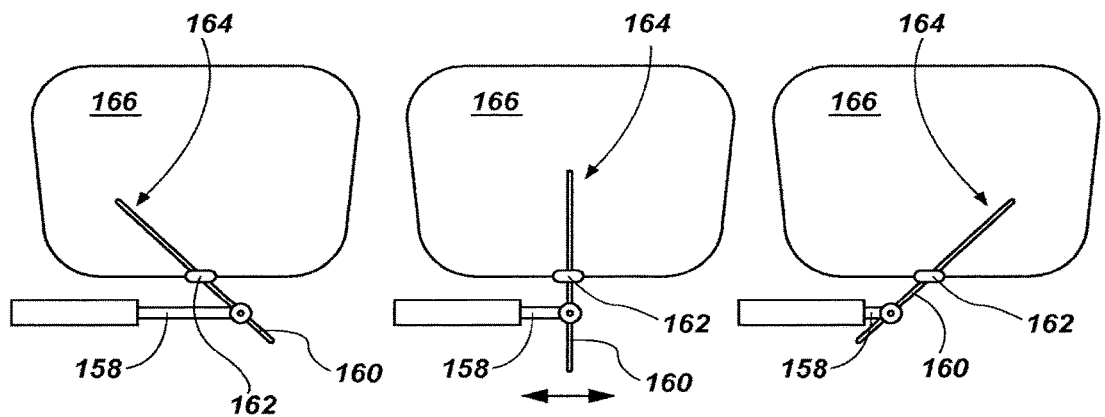
FIG. 23     FIG. 24     FIG. 25
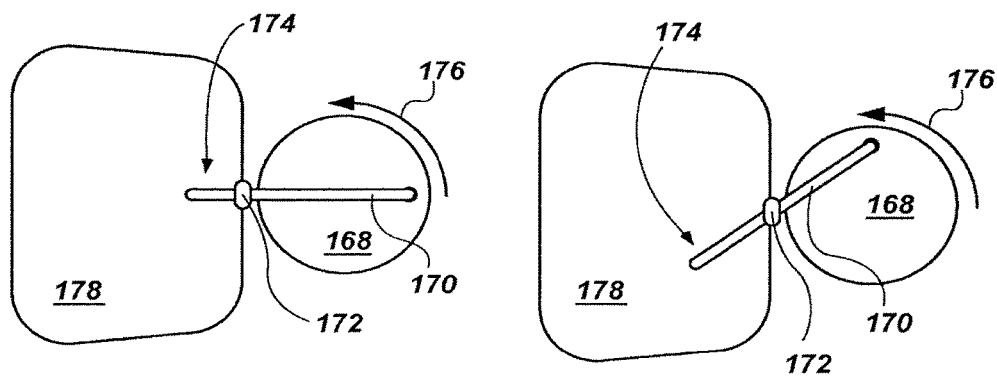
FIG. 26     FIG. 27
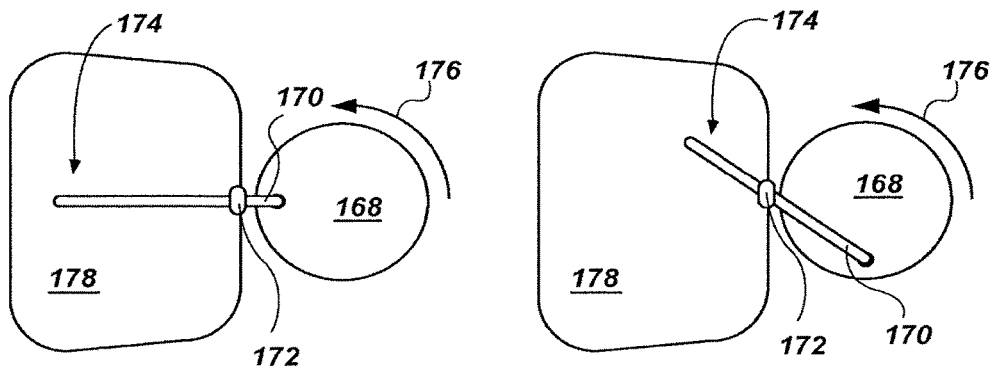
FIG. 28     FIG. 29

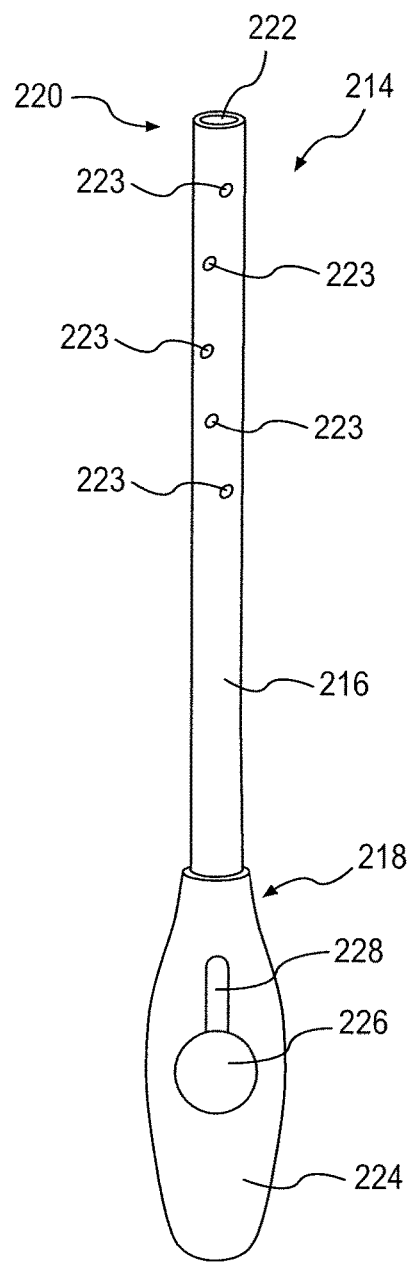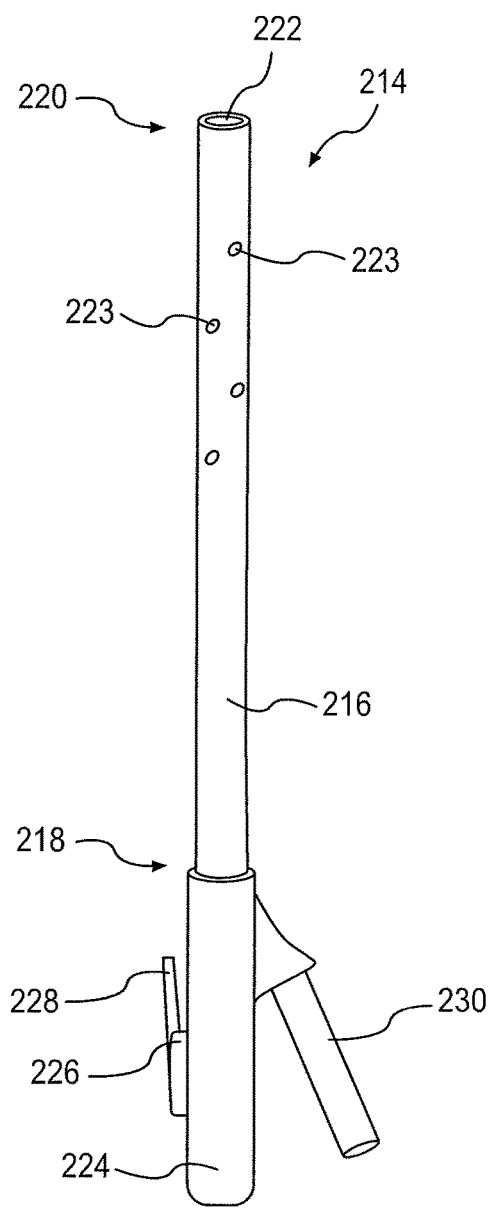
FIG. 42
FIG. 43

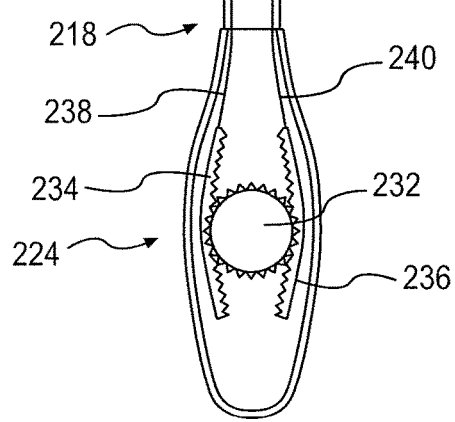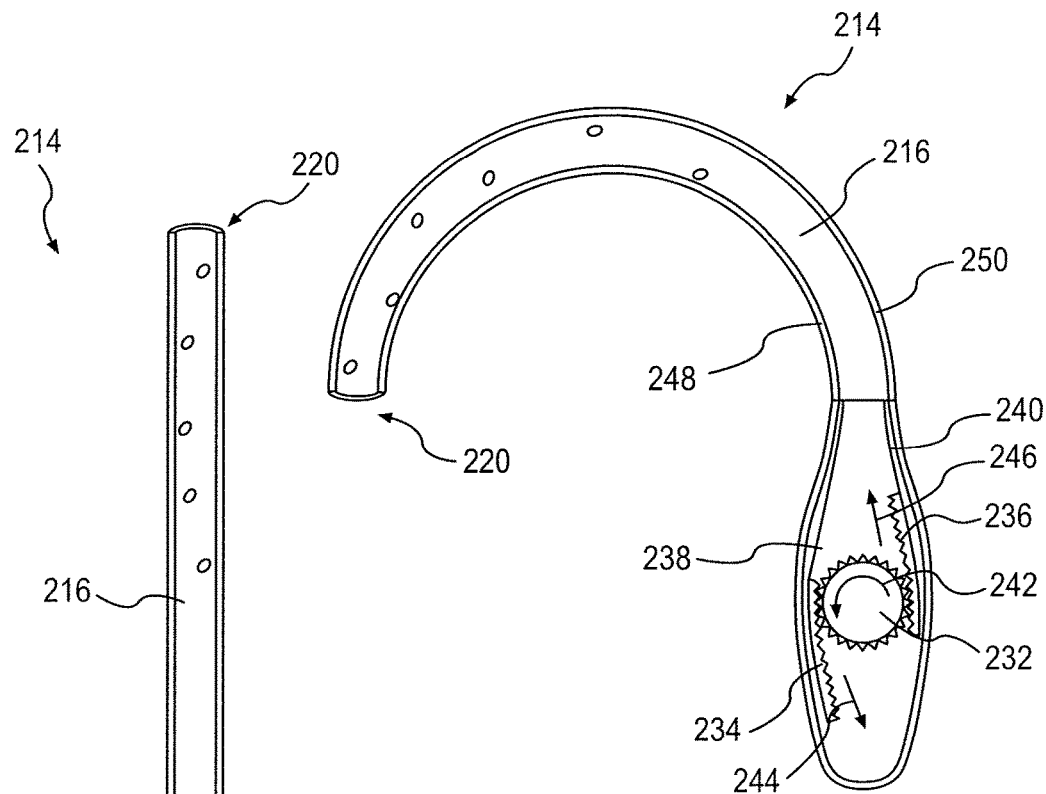
FIG. 44
FIG. 45

BODY CAVITY DRAINAGE DEVICES AND RELATED METHODS

CROSS-REFERENCE TO RELATED APPLICATIONS

This application is a continuation-in-part of U.S. patent application Ser. No. 13/045,274, which claims the benefit of U.S. Provisional Application Ser. No. 61/312,878, filed Mar. 11, 2010, entitled "BODY CAVITY DRAINAGE DEVICE AND RELATED METHODS," the disclosure of each of which is hereby incorporated herein by this reference in its entirety.

BACKGROUND

Field

Embodiments of the invention relate to body cavity drainage devices and related methods.

State of the Art

Drainage devices, especially for the evacuation of a pleural cavity, may consist of a hollow flexible tube inserted through an incision into the pleural cavity. The shape and configuration of the pleural cavity often necessitates multiple incisions to be made to permit the drainage tube to reach various locations in the pleural cavity. The need for multiple incisions may generally result in an extended hospital stay from a patient suffering from a severe case of pleurisy.

BRIEF SUMMARY

In some embodiments, a body cavity drainage device for a patient may comprise a drainage tube and an activation device. The drainage tube may have a proximal end and a distal end and a length sufficient to extend the distal end into the body cavity with the proximal end external to the patient. The activation device may be at least partially external to the patient for attachment to the proximal end of the drainage tube and adapted and structured to move the distal end of the drainage tube within a body cavity.

In additional embodiments, a body cavity drainage device may comprise a drainage tube having a proximal end and a distal end, and an automated means to move the distal end of the device about a body cavity of a patient.

In further embodiments, a body cavity drainage device may comprise a drainage tube that includes at least one open lumen having at least one opening at a proximal end and at least one opening at a distal end, and at least one closed lumen having at least one opening at a proximal end and a closed distal end.

In additional embodiments, a body cavity drainage device may comprise a drainage tube having a distal end sized and configured for insertion into a body cavity, a sleeve sized and configured to couple to a body cavity wall sealingly coupled with the drainage tube and slidable relative thereto, the distal end of the drainage tube positioned at a first side of the sleeve. The body cavity drainage device may further include a motion generator positioned on a second side of the sleeve and coupled to the drainage tube to effectuate movement of the distal end of the drain tube.

In further embodiments, a body cavity drainage device may comprise a drainage tube having a proximal end and a distal end, a first lumen and a second lumen. The first lumen may have at least one opening at the distal end and may be coupled to a suction source at the proximal end. The second lumen may have at least one opening at the distal end and may be coupled to a pressurized fluid source.

In yet further embodiments, methods of providing a treatment within a body cavity may comprise positioning a distal end of a drainage tube within the body cavity, and automatically moving the distal end of the drainage tube within the body cavity.

BRIEF DESCRIPTION OF THE SEVERAL VIEWS OF THE DRAWINGS

FIG. 4 shows a cross-sectional view of a drainage tube including a plurality of closed lumens, according to an additional embodiment of the present disclosure.

FIG. 5 shows a detail view of a distal end portion of the drainage tube of FIG. 4, wherein a closed lumen is filled with a pressurized fluid.

FIG. 6 shows a detail view of a distal end portion of the drainage tube of FIG. 4, wherein a different closed lumen is filled with a pressurized fluid.

FIG. 23 shows a schematic view of a linear motion generator in a fully extended state coupled to a drainage tube inserted into a body cavity, according to an embodiment of the present invention.

FIG. 24 shows a schematic view of the linear motion generator, drainage tube and body cavity of FIG. 23, wherein the linear motion generator is in a partially extended state.

FIG. 25 shows a schematic view of the linear motion generator, drainage tube and body cavity of FIG. 23, wherein the linear motion generator is in a retracted state.

FIG. 26 shows a schematic view of a circular motion generator in a first position coupled to a drainage tube inserted into a body cavity, according to an embodiment of the present invention.

FIG. 27 shows a schematic view of the circular motion generator, drainage tube and body cavity of FIG. 26, wherein the circular motion generator has been rotated one-quarter revolution.

FIG. 28 shows a schematic view of the circular motion generator, drainage tube and body cavity of FIG. 26, wherein the circular motion generator has been rotated one-half revolution.

FIG. 29 shows a schematic view of the circular motion generator, drainage tube and body cavity of FIG. 26, wherein the circular motion generator has been rotated three-quarters revolution.

FIG. 42 shows a top view of a drainage device according to an embodiment of the present disclosure.

FIG. 43 shows a side view of the drainage device of FIG. 42.

FIGS. 44 and 45 show cross-sectional views of the drainage device of FIG. 42.

DETAILED DESCRIPTION

In some embodiments, a drainage device may include a drainage tube configured to change shape in response to fluid pressure to facilitate the movement of a distal end thereof.

Figure 1:
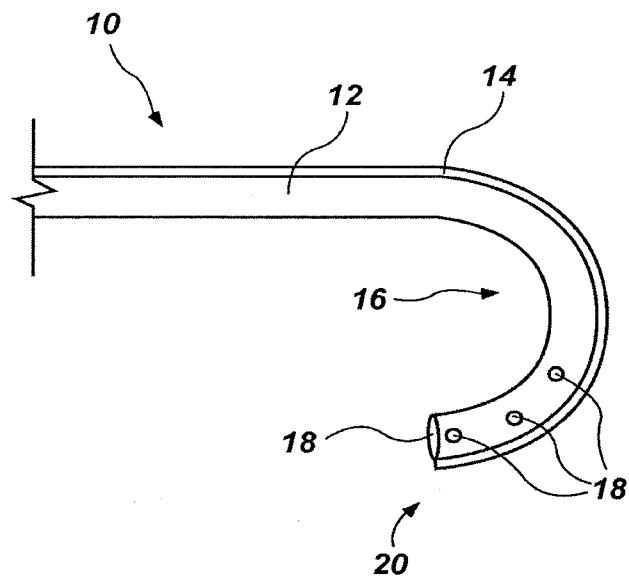
FIG. 1 shows a detail view of a distal end portion of a drainage tube in a relaxed state, according to an embodiment of the present disclosure.

In one embodiment, as shown in FIG. 1, a drainage tube 10 may be generally configured as a catheter and may include a plurality of lumens. For example, the drainage tube 10 may include an open lumen 12 and a closed lumen 14. The drainage tube may further include a biasing structure 16, such as an elastic material region (e.g., flexible material region).

The open lumen 12 may include at least one opening 18 proximate to a first distal end 20 thereof and, in some embodiments, may include a plurality of openings 18 proximate to the first distal end 20. The one or more openings 18 may be defined by a one or more of apertures, porous regions, and other fluid permeable structures. The open lumen 12 may additionally include an opening at an opposing, second distal end that may be selectively coupled to a suction source, such as a vacuum (not shown).

The biasing structure 16 may be defined by an elastically deformable wall of the drainage tube 10. As a non-limiting example, the biasing structure 16 may bias the drainage tube 10 to extend along a generally arcuate path, such as shown in FIG. 1. In further embodiments, a biasing structure 16 may bias a drainage tube 10 to extend along a spiral path (not shown). In yet additional embodiments, a biasing structure 16 may bias a drainage tube 10 to extend along another path, such as a path having a generally linear shape.

Figure 2:
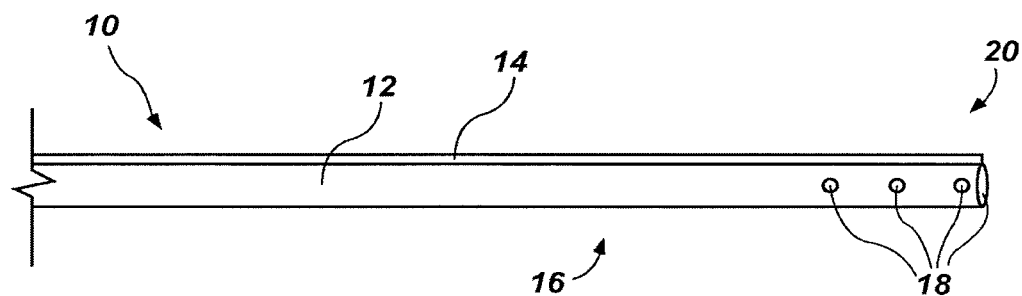
FIG. 2 shows a detail view of the distal end portion of the drainage tube shown in FIG. 1, wherein a closed lumen is filled with a pressurized fluid.
Figure 3:
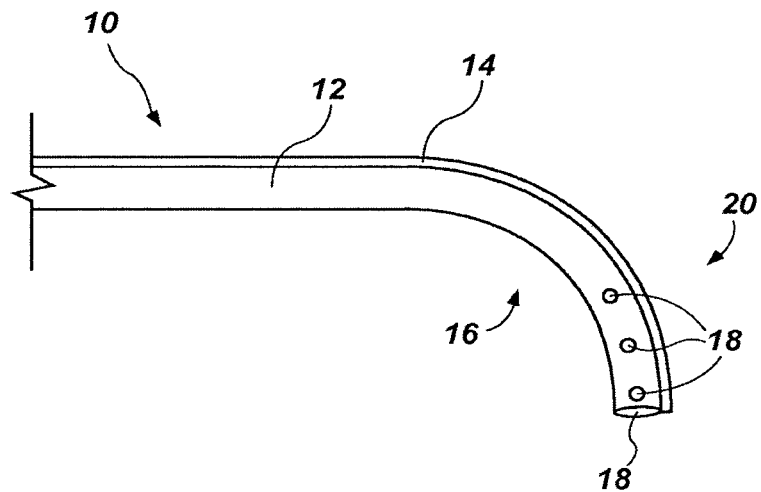
FIG. 3 shows a detail view of the distal end portion of the drainage tube shown in FIG. 1, wherein the fluid within the closed lumen is at an intermediate pressure.

The closed lumen 14 may extend longitudinally along at least a portion of the open lumen 12. In some embodiments, such as shown in FIG. 1, the closed lumen 14 may extend along the open lumen 12 and a closed, distal end of the closed lumen 14 may be at least proximate to the distal end of the open lumen 12. The closed lumen 14 may additionally include an opening at an opposing, proximal end that may be selectively coupled to a fluid pressure source, such as a piston pump (e.g., a syringe) (not shown). When fluid within the interior of the closed lumen 14 is at a pressure at or near ambient pressure, the drainage tube 10 may be biased into a first path, such as a non-linear path (e.g., a generally arcuate path). However, as the fluid pressure within the closed lumen 14 is increased above the ambient pressure, such as by inflation with a gas (i.e., air) or insertion of a liquid (i.e., water), the closed lumen 14 may change in shape and cause the drainage tube 10 to extend along a different second path, such as a substantially linear path as shown in FIG. 2. In view of this, the shape of the drainage tube 10, and thus the position of the distal end 20 thereof, may be affected by varying the fluid pressure within the closed lumen 14. Conversely, when fluid within the interior of the closed lumen 14 is at a pressure at or near ambient pressure, the drainage tube 10 may be biased into a first path, such as a linear path. However, as the fluid pressure within the closed lumen 14 is increased above the ambient pressure, such as by inflation with a gas (i.e., air) or insertion of a liquid (i.e., water), the closed lumen 14 may change in shape and cause the drainage tube 10 to extend along a different second path, such as a substantially non-linear path (e.g., a generally arcuate path) as shown in FIG. 1. Additionally, by applying an intermediate fluid pressure within the closed lumen 14, the drainage tube 10 may assume an intermediate shape, such as shown in FIG. 3.

In additional embodiments, a drainage tube 22 may include an open lumen 24 for drainage and a plurality of closed lumens 26, 28, 30, 32 configured to facilitate the selective movement of a distal end in a number of directions in response to fluid pressure, as shown in cross-section in FIG. 4. For example, the drainage tube 22 may be biased along a generally linear path when the fluid within each closed lumen 26, 28, 30, 32 is at or near ambient pressure. When fluid pressure is applied to a first closed lumen 26 the first closed lumen 26 may change shape, such as a shape extending along a generally arcuate path, and facilitate the movement of the distal end 34 of the drainage tube 22, having openings 36 therein, in a first direction 38, as indicated in FIG. 4 and as shown in FIG. 5. When fluid pressure is applied to a second closed lumen 28 the second closed lumen 28 may change shape, such as a shape extending along another generally arcuate path, and facilitate the movement of the distal end 34 of the drainage tube 22 in a second direction 40, generally opposite the first direction 38, as indicated in FIG. 4 and as shown in FIG. 6. Similarly, when fluid pressure is applied to a third closed lumen 30 the third closed lumen 30 may change shape, such as a shape extending along yet another generally arcuate path, and facilitate the movement of the distal end of the drainage tube in a third direction 42, generally perpendicular to the first direction 38 and second direction 40, as indicated in FIG. 4. Finally, when fluid pressure is applied to a fourth closed lumen 32 the fourth closed lumen 32 may change shape and facilitate the movement of the distal end 34 of the drainage tube 22 in a fourth direction 44, generally opposite to the third direction 42, as indicated in FIG. 4.

In additional embodiments, an elongated structure may be utilized, rather than fluid pressure, to effectuate movement of a distal end of a drainage tube. For example, a wire or rod may be inserted into a closed lumen to change the shape thereof and facilitate movement of the distal end of the drainage tube.

In some embodiments, at least one wire may be attached at or near a distal end of a drainage tube to effectuate the movement thereof, such as shown in FIGS. 7-15. As such embodiments may not utilize fluid pressure; such embodiments may not include any closed lumens. As used herein, the term "wire" is a broad term that encompasses any type of flexible elongated material capable of providing a pulling force and encompasses, by way of example and not limitation, metal wire, coated wire, polymer wire, woven or braided wire, string, yarn, line, cable, filament, lace, and cord.

Figure 7:
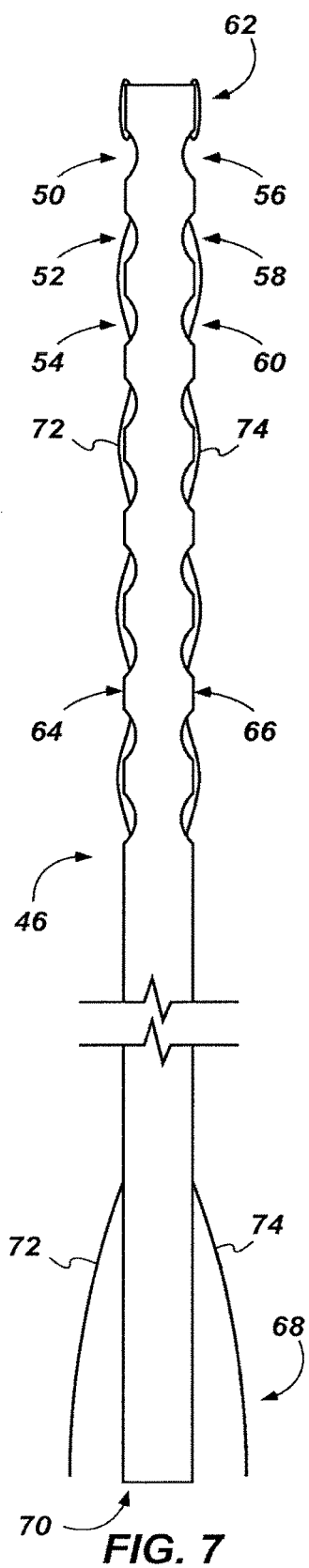
FIG. 7 shows front view of a drainage tube including wires attached to the distal end of the drainage tube, according to an embodiment of the present disclosure.
Figure 8:
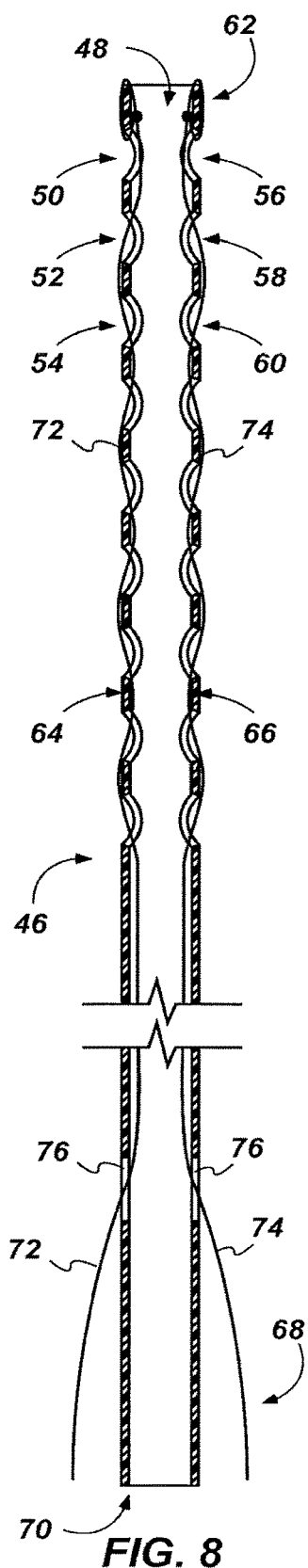
FIG. 8 shows a cross-sectional view of the drainage tube of FIG. 7.
Figure 9:
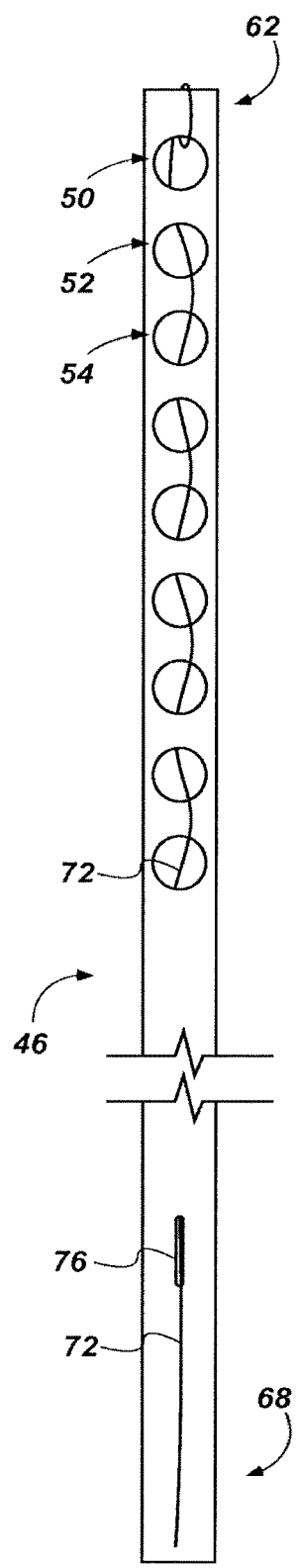
FIG. 9 shows a side view of the drainage tube of FIG. 7.

In some embodiments, such as shown in FIGS. 7-9, a drainage tube 46 may be comprised of a single open lumen forming a central passage 48 (FIG. 8) through the drainage tube 46. The drainage tube 46 may be formed of a flexible material, such as a flexible polymer material, and may include a plurality of openings 50, 52, 54, 56, 58, 60 near a distal end 62. The drainage tube 46 may include a first plurality of openings 50, 52, 54 to the central passage 48 along a first side 64 of the drainage tube 46 near the distal end 62. The drainage tube 46 may also include a second plurality of openings 56, 58, 60 to the central passage 48 along an opposing, second side 66 of the drainage tube 46 near the distal end 62. A proximal end 68 of the drainage tube 46 may include an opening 70 configured for attachment to a vacuum source.

A first wire 72, such as a nickel titanium wire (e.g., a nitinol wire) having a polytetrafluoroethylene (e.g., TEFLON®) coating, may be attached to the drainage tube 46 at or near the distal end 62 of the drainage tube 46 and may be woven through the first plurality of openings 50, 52, 54. For example, the first wire 72 may extend from an outside surface of the drainage tube 46 and into the central passage 48 of the drainage tube 46 through a first opening 50 of the first plurality of openings 50, 52, 54. The first wire 72 may then extend along the central passage 48 for a distance and then extend to the outside of the drainage tube 46 through a second opening 52 of the first plurality of openings 50, 52, 54. The first wire 72 may then extend along the outside of the drainage tube 46 for another distance and extend back into the central passage 48 of the drainage tube 46 through a third opening 54 of the first plurality of openings 50, 52, 54. The first wire 72 may be woven in a similar manner through any number of additional openings formed along a first side 64 of the drainage tube 46. The first wire 72 may then extend through the central passage 48 of the drainage tube 46 toward the proximal end 68 of the drainage tube 46 and may extend out of the drainage tube 46 at or near the proximal end 68 of the drainage tube 46.

Similarly, an opposing, second wire 74, such as a nickel titanium wire (e.g., a nitinol wire) having a polytetrafluoroethylene (e.g., TEFLON®) coating, may be attached to the drainage tube 46 at or near the distal end 62 of the drainage tube 46 and may be woven through the second plurality of openings 56, 58, 60. For example, the second wire 74 may extend from an outside surface of the drainage tube 46 and into the central passage 48 of the drainage tube 46 through a first opening 56 of the second plurality of openings 56, 58, 60. The second wire 74 may then extend along the central passage 48 for a distance and then extend to the outside of the drainage tube 46 through a second opening 58 of the second plurality of openings 56, 58, 60. The second wire 74 may then extend along the outside of the drainage tube 46 for another distance and extend back into the central passage 48 of the drainage tube 46 through a third opening 60 of the second plurality of openings 56, 58, 60. The second wire 74 may be woven in a similar manner through any number of additional openings formed along a second side 66 of the drainage tube 46. The second wire 74 may then extend through the central passage 48 of the drainage tube 46 toward the proximal end 68 of the drainage tube 46 and may extend out of the drainage tube 46 at or near the proximal end 68 of the drainage tube 46.

As shown in FIGS. 7-9, the first and second wires 72, 74 may extend out of the drainage tube 46 through relatively small openings 76 near the distal end 68 of the drainage tube 46. Optionally, the first and second wires 72, 74 may extend out of the drainage tube 46 through openings 76 that provide a fluid seal around the first and second wires 72, 74. In view of this, there may be little or no leakage of ambient air into the drainage tube 46 through such openings 76 during operation thereof.

Figure 10:
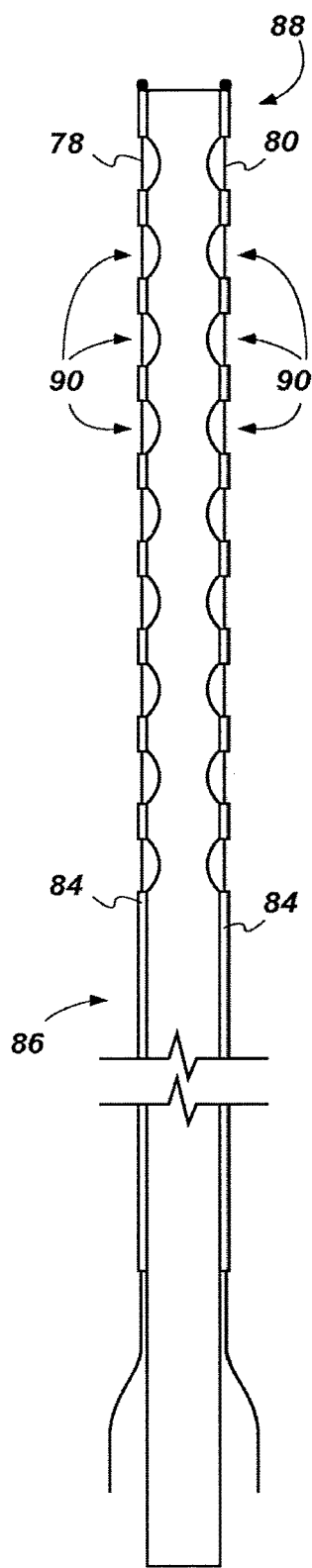
FIG. 10 shows front view of a drainage tube including wires attached to the distal end of the drainage tube and routed through lumens, according to an embodiment of the present disclosure.
Figure 11:
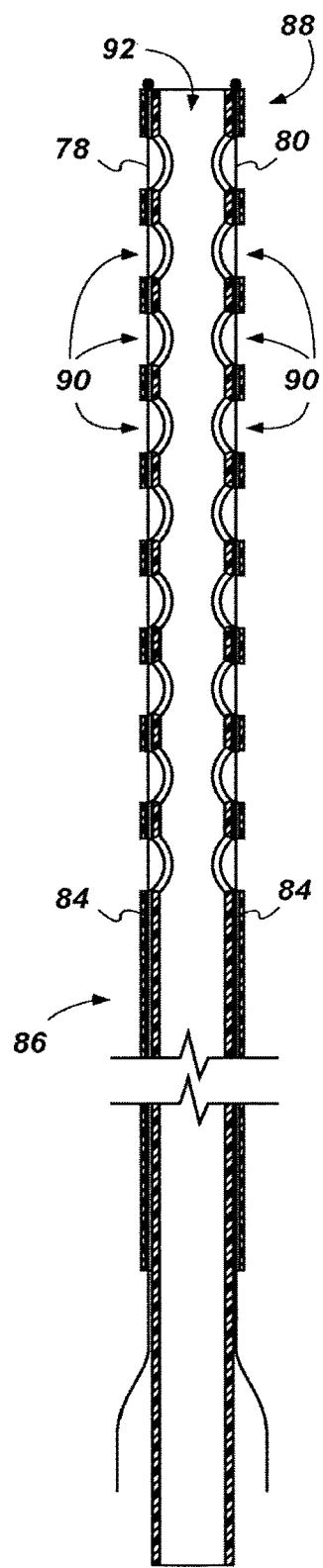
FIG. 11 shows a cross-sectional view of the drainage tube of FIG. 10.
Figure 12:
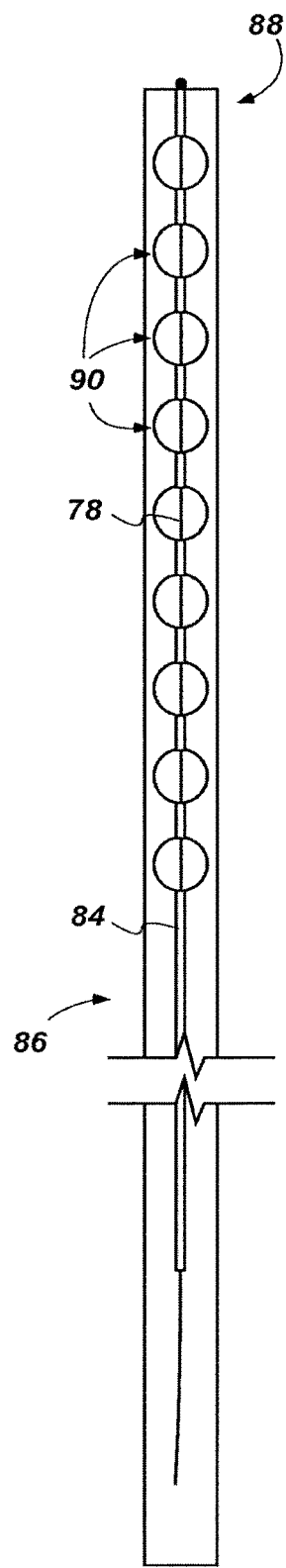
FIG. 12 shows a side view of the drainage tube of FIG. 10.

In additional embodiments, as shown in FIGS. 10-12, a first wire 78 and a second wire 80 may be inserted into relatively small lumens 82, 84 that are separate from a primary open lumen of a drainage tube 86 and the first and second wires 78, 80 may be attached to a distal end 88 of the drainage tube 86. In such embodiments, openings 90 into a central passage 92 of the drainage tube 86 may extend through the lumens 82, 84, creating a plurality of lumen 82, 84 segments. In view of this, the first and second wires 78, 80 may be exposed at the openings 90 into the central passage 92 of the drainage tube 86. As shown in FIGS. 10-12, the lumens 82, 84 and wires 78, 80 may be positioned on opposing sides of the drainage tube 86.

Figures 13, 14, 15:
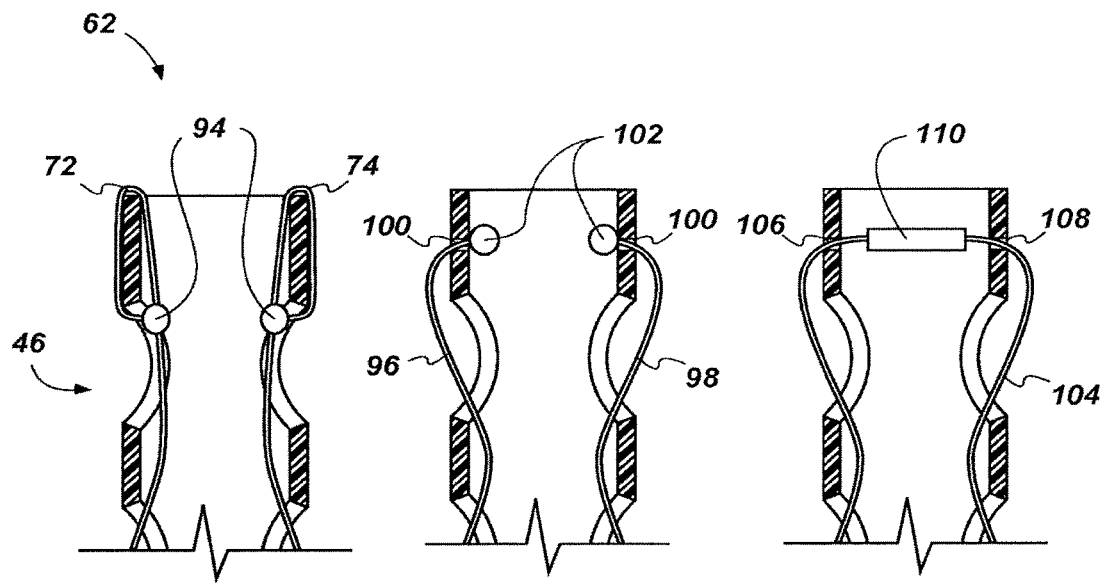
FIG. 13 shows a cross-sectional detail view of a distal end of a drainage tube including wires surrounding a portion of the distal end.
FIG. 14 shows a cross-sectional detail view of a distal end of a drainage tube including wires with stops thereon.
FIG. 15 shows a cross-sectional detail view of a distal end of a drainage tube including a single wire with a stop thereon.

For embodiments that include wires, such as shown in FIGS. 7-12, the attachment of the wire 72, 74, 78, 80 to the drainage tube 46, 86 at or near the distal end 62, 88 may be accomplished by one of any number of attachment configurations. For example, each wire 72, 74 may wrap around a portion of the distal end 62 of the drainage tube 46, as shown in FIG. 13. Each wire 72, 74 may then be attached to itself at a joint 94, such as by a weld joint, a swaged or crimped joint, a knot, or another joint. For another example, a first wire 96 and a second wire 98 may extend through an opening 100 sized similar to a diameter of each respective wire 96, 98 and a stop 102, such as a weld bead or a swaged member, may be attached to a free end of each wire 96, 98 to prevent the free end of each wire 96, 98 from passing through the openings 100, respectively, such as shown in FIG. 14. In yet further embodiments, a single cable 104 may be utilized as a first cable and a second cable, such as shown in FIG. 15. When a single cable 104 is used the cable 104 may extend through first opening 106 and second opening 108 sized similar to a diameter of the wire 104 and a stop 110, such as a weld bead or a swaged member, may be attached to the cable 104 at a location between the first opening 106 and the second opening 108.

Figure 16:
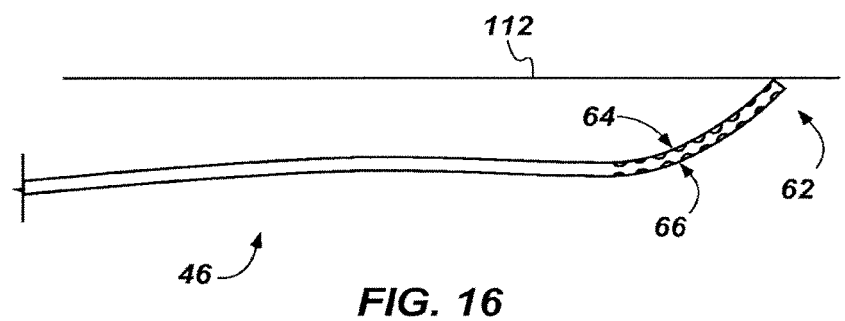
FIG. 16 shows a schematic view of a drainage tube with wires, such as shown in FIGS. 7 and 10, in operation.
Figure 17:
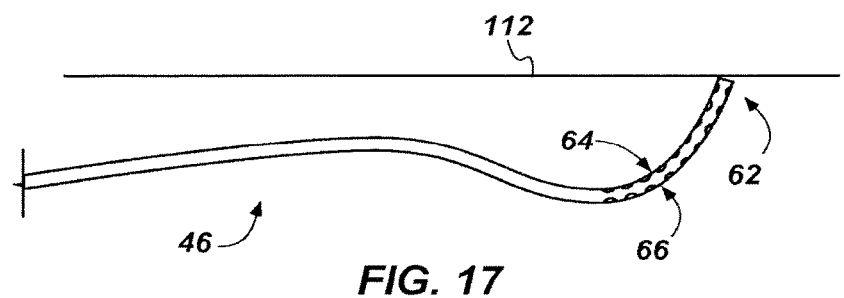
FIG. 17 shows a schematic view of the drainage tube of FIG. 16 moved to a second position.

In operation, the distal ends 62, 88 of drainage tubes 46, 86 including wires 72, 74, 78, 80, such as shown in FIGS. 7-12, may be moved by the manipulation of the wires 72, 74, 78, 80 at the proximal end 68 of the drainage tube 46, 86. For example, as shown in FIGS. 16 and 17, and as described with further reference to features shown in FIGS. 7-10, when a tensile force is applied to the first wire 72 (e.g., when a pulling force is applied to the first wire 72 from the proximal end 68) the first side 64 of the drainage tube 46 may be put into compression. When the first side 64 of the drainage tube 46 is put into compression, the drainage tube 46 may flex at locations where the first plurality of openings 50, 52, 54 is located and the drainage tube 46 may bend in a first direction, as shown in FIGS. 16 and 17. Similarly, when a tensile force is applied to the second wire 74 (e.g., when a pulling force is applied to the second wire 74 from the proximal end 68) the second side 66 of the drainage tube 46 may be put into compression. When the opposing, second side 66 of the drainage tube 46 is put into compression the drainage tube may flex at locations where the second plurality of openings 56, 58, 60 is located and the drainage tube 46 may bend in an opposing, second direction (not shown). In view of this, the number of openings 50, 52, 54, 56, 58, 60 and the position of the openings 50, 52, 54, 56, 58, 60 in the drainage tube 46 may be chosen to cause the drainage tube 46 to exhibit a desired change in shape upon manipulation of the wires 72, 74 from the proximal end 68.

Additionally, when the distal end 62 of the drainage tube 46 contacts an obstruction 112, the distal end 62 of the drainage tube 46 may remain in contact with the edge of the obstruction 112 as the drainage tube 46 continues to flex, as shown in FIGS. 16 and 17. This may allow the edges of a body cavity, or the edges of an object within the body cavity, to be efficiently cleared of fluids and improve the drainage of the body cavity.

Figure 18:
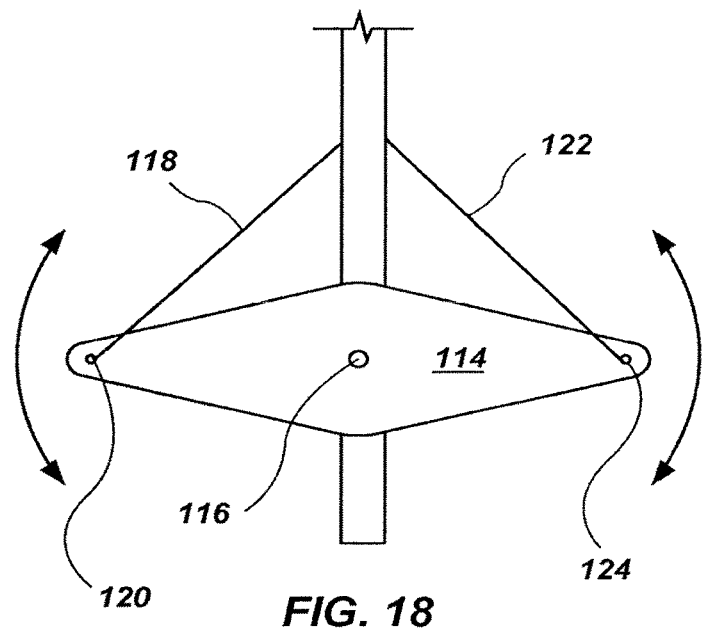
FIG. 18 shows a schematic view of a device for operating the wires of a drainage tube with wires, such as shown in FIGS. 7 and 10, including a yoke.
Figure 19:
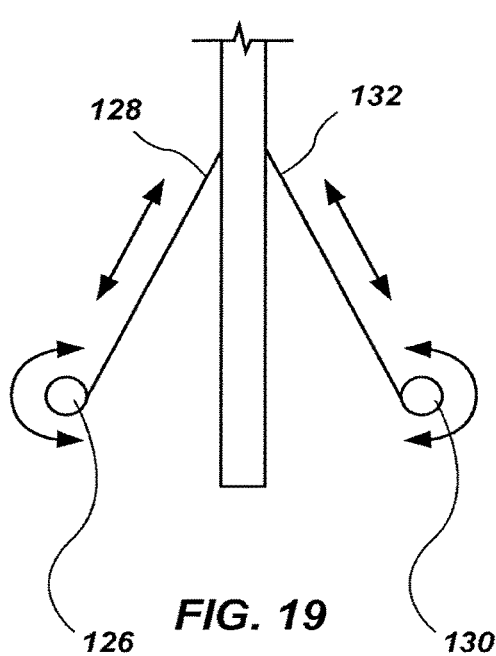
FIG. 19 shows a schematic view of a device for operating the wires of a drainage tube with wires, such as shown in FIGS. 7 and 10, including separate reels.
Figure 20:
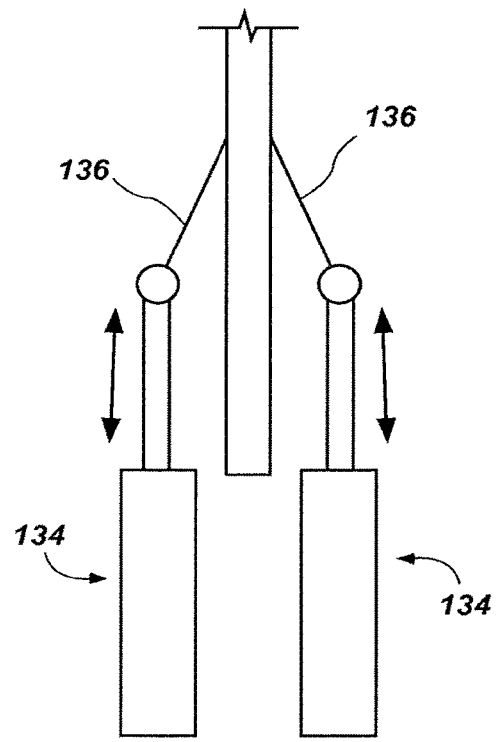
FIG. 20 shows a schematic view of a device for operating the wires of a drainage tube with wires, such as shown in FIGS. 7 and 10, including linear actuators.

For drainage tubes including wires, such as shown in FIGS. 7-12, any number of mechanisms may be attached to the proximal ends of the wires to selectively apply tensile force to the wires. In some embodiments, the proximal ends of the wires may be manipulated directly by a physician. In further embodiments, the wires may be manipulated automatically by a programmed device. For example, in some embodiments a motor (not shown) may be attached to a yoke 114 at a central location 116 thereof, such as shown in FIG. 18. When the motor is turned in a first direction, a first wire 118 may be pulled by the yoke 114 and a tensile force may be applied to the first wire 118, which may be attached at a first end 120 of the yoke 114. Similarly, when the motor is turned in an opposing, second direction, a second wire 122 may be pulled by the yoke 114 and a tensile force may be applied to the second wire 122, which may be attached to a second end 124 of the yoke 114. In additional embodiments, a first reel 126 may be attached to a first wire 128 and a second reel 130 may be attached to a second wire 132, and motors (not shown) attached to each reel 126, 130 and may selectively apply a tensile force to each wire 128, 132, respectively, such as shown in FIG. 19. In yet further embodiments, a linear actuator 134, such as a pneumatic, hydraulic, or electric linear actuator, may be attached to each wire 136 and may selectively apply a tensile force to each wire 136, respectively, such as shown in FIG. 20.

Although the embodiments shown in FIGS. 7-20 include a first wire and a second wire, different numbers of wires may be utilized. For example, a drainage tube may include only a first wire and not include a second wire. Additionally, a drainage tube may include a first wire, a second wire, and any number of additional wires. Generally, the more wires that are included, the greater the range of motion that may be achieved with a distal end of a drainage tube. However, two opposing wires may provide sufficient range of motion for many therapeutic uses, such as for draining fluid from a body cavity, such as a pleural cavity.

Figure 21:
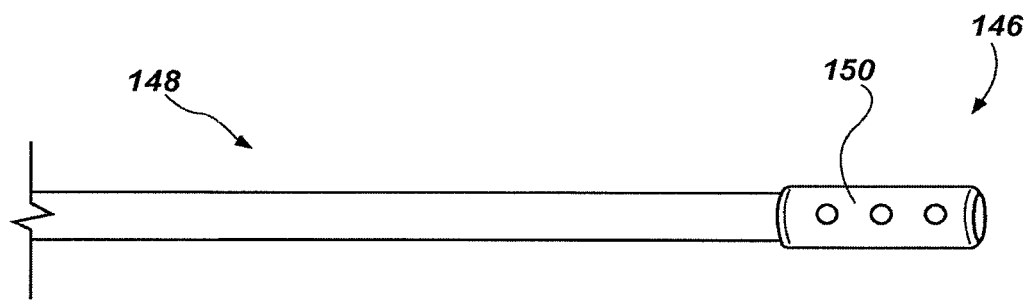
FIG. 21 shows a detail view of a distal end portion of a drainage tube including a magnetic end portion, according to an embodiment of the present invention.
Figure 22:
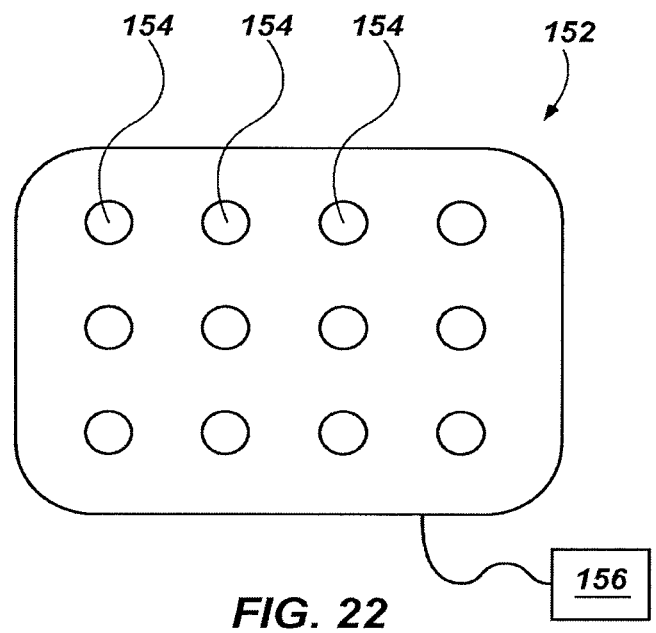
FIG. 22 shows a schematic view of a magnetic field generator, according to an embodiment of the present invention.

In additional embodiments, such as shown in FIG. 21, movement of a distal end 146 of a drainage tube 148 may be facilitated by an applied magnetic force, which may be generated outside of a patient's body. In such embodiments, the drainage tube 148 may include a magnetic material portion (i.e., a material that may experience a force in response to an applied magnetic field), such as a ferromagnetic material portion (e.g., iron, nickel, cobalt, gadolinium, neodymium, samarium and alloys thereof). For example, the drainage tube 148 may include a magnetic structure 150 formed of a magnetic material positioned near the distal end 146 thereof, such as shown in FIG. 16. The magnetic structure 150 may be formed of a material that is different than a majority of the drainage tube 148, or may be defined by a region doped with a magnetic material. In view of this, a magnetic force may be applied to the distal end 146 of the drainage tube 148 by the application of a magnetic field generating device 152, such as shown in FIG. 22, which may cause the distal end 146 of the drainage tube 148 to move in response thereto.

In some embodiments, the magnetic field generating device 152 may be configured as an external covering that may be worn by a patient (e.g., as a vest) or may be draped over the patient. The magnetic field generating device 152 may deliver a reconfigurable magnetic field that may cause the distal end 146 of a drainage tube 148 positioned within a body cavity, such as a pleural cavity of a patient, to move about the body cavity. For example, the magnetic field generating device 152 may include a plurality of temporary magnets 154 (e.g., electromagnets), distributed thereabout that may be selectively activated to generate a number of magnetic field configurations to affect the movement of the distal end 146 of the drainage tube 148 to a number of positions within the body cavity. In additional embodiments, a magnetic field generating device may include permanent magnets that may be utilized to generate a number of magnetic field configurations. For example, a permanent magnet may be moved about or the orientation of a plurality of permanent magnets relative to one another may be manipulated to generate different magnetic field configurations. Additionally, the magnetic field generation may be automatically activated and manipulated, such as by a programmed control module 156.

In additional embodiments, motion generators positioned external to a patient may facilitate movement of a distal end of a drain tube positioned within a body cavity of the patient.

In some embodiments, a linear motion generator, such as a piston 158, may be attached to a drainage tube 160, such as shown in FIGS. 23 through 25. In such embodiments, the drainage tube 160 may be positioned within a sleeve 162 that may be positioned within a cavity wall, such as a chest wall, of a patient. A distal end 164 of the drainage tube 160 may be positioned within a body cavity 166 at a first side of the sleeve 162 and the piston 158 may be coupled to the drainage tube 160 at an opposing, second side of the sleeve 162. The sleeve 162 may be configured to allow the movement of the drainage tube 160 relative to the sleeve 162, and thus relative to the patient's cavity wall as the sleeve 162 may be configured to contact and be coupled to the patient's cavity wall, while maintaining a seal between the sleeve 162 and the drainage tube 160. In view of this, in some embodiments, the distal end 164 of the drainage tube 160 may be inserted into a body cavity of a patient, such as a pleural cavity, and an outer wall of the sleeve 162 may be coupled to the chest wall of the patient. Upon insertion, the piston 158 may be extended and/or retracted to facilitate movement of the distal end 164 of the drainage tube 160 within the patient's body cavity 166, as shown in FIGS. 23 through 25.

In additional embodiments, a circular motion generator, such as a wheel 168 attached to a motor, may be attached to a drainage tube 170, such as shown in FIGS. 26 through 29. In such embodiments, the drainage tube 170 may be positioned within a sleeve 172 that may be positioned within a cavity wall, such as a chest wall, of a patient. A distal end 174 of the drainage tube 170 may be positioned at a first side of the sleeve 172 and the wheel 168 may be coupled to the drainage tube 170 at an opposing, second side of the sleeve 172. The sleeve 172 may be configured to allow the movement of the drainage tube 170 relative to the sleeve 172, and thus relative to the patient's cavity wall as the sleeve 172 may be configured to contact and be coupled to the patient's cavity wall, while maintaining a seal between the sleeve 172 and the drainage tube 170. In view of this, in some embodiments, the distal end 174 of the drainage tube 170 may be inserted into a body cavity of a patient, such as a pleural cavity, and an outer wall of the sleeve 172 may be coupled to the chest wall of the patient. Upon insertion, the wheel 168 may be selectively rotated, such as in a direction indicated by the arrow 176, to facilitate movement of the distal end 174 of the drainage tube 170 within a patient's body cavity 178, as shown in FIGS. 26 through 29.

In embodiments utilizing motion generators external to a patient, or other embodiments wherein a portion of a drainage tube may be inserted and/or retracted from the patient outside of a sterile environment, at least a portion of the drainage tube may be covered by a flexible covering that may be attached to the sleeve, such as a flexible plastic film (not shown).

Although linear and circular motion generators have been shown and described in particular embodiments herein, other motion generators, as will be recognized by a person of ordinary skill in the art, may also be utilized to generate other simple motions or compound motions.

Figure 30:
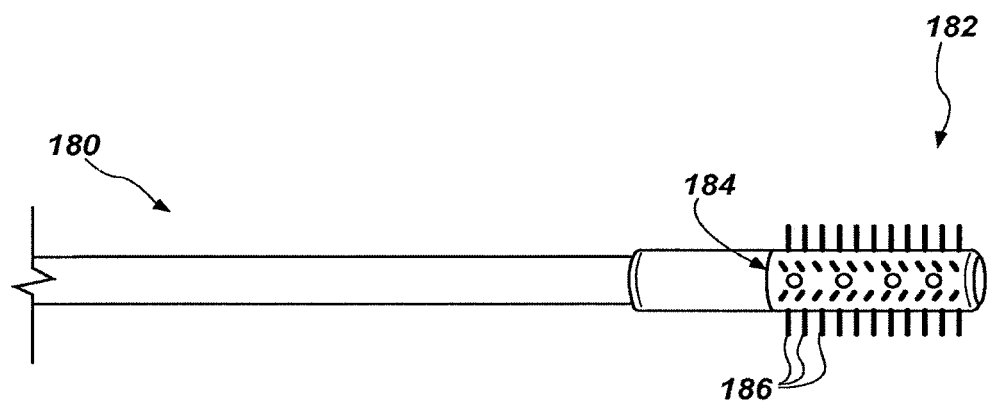
FIG. 30 shows a detail view of a distal end portion of a drainage tube including a rotatable end portion, according to an embodiment of the present disclosure.

In additional embodiments, a drainage tube 180 may include a locomotion device positioned at least proximate to a distal end 182 thereof. For example, the drainage tube may include a distal end portion 184 that is rotatable, as shown in FIG. 30. Optionally, the rotatable distal end portion 184 may further include protrusions 186 laterally extending from a surface thereof, such as similar to relatively soft bristles of a brush. In view of this, upon the selectable rotation of the rotatable distal end portion 184, the distal end 182 of the drainage tube 180 may move about a body cavity, such as a pleural cavity. Additionally, the protrusions 186 may be utilized to massage internal body tissue, such as lung tissue. The locomotion device may be powered by electric power, hydraulic power, or another power source. As non-limiting examples, power may be provided by directing electricity through a wire positioned within the drainage tube 180 or by directing fluid through lumens of the drainage tube 180, such as by fluid injection or by fluid suction. Although a rotatable end portion 184 is shown and described with reference to FIG. 30, other locomotion devices may be positioned at least proximate to a distal end 182 of the drainage tube 180 to provide locomotion of the distal end 182 of the drainage tube 180 relative to a patient's body cavity. For example, any number of mechanical device configurations (e.g., a microelecromechanical system (MEMS)) may be utilized to provide mechanical locomotion, such as including rotatable wheels, articulated legs, and other mechanisms.

Figure 31:
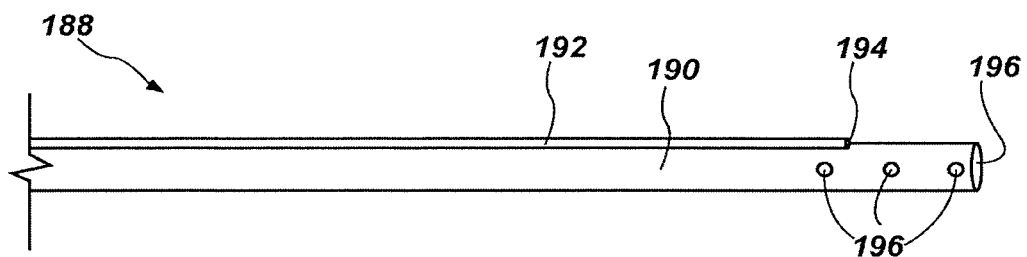
FIG. 31 shows a detail view of a distal end portion of a drainage tube including a separate open lumen, according to an embodiment of the present disclosure.
Figure 32:
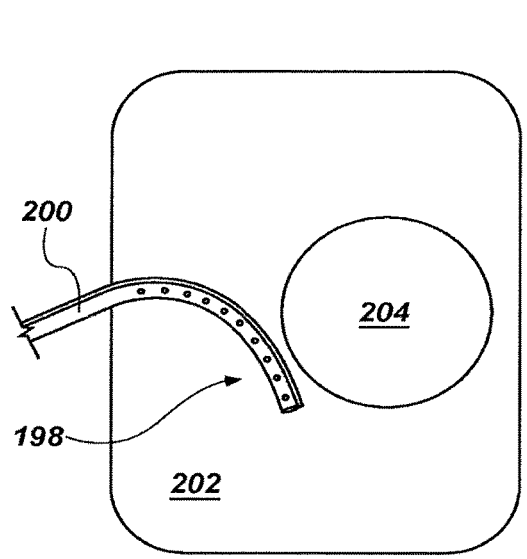
FIG. 32 shows a schematic detail view of a drainage tube having a distal end in a first position within a pleural cavity.
Figure 33:
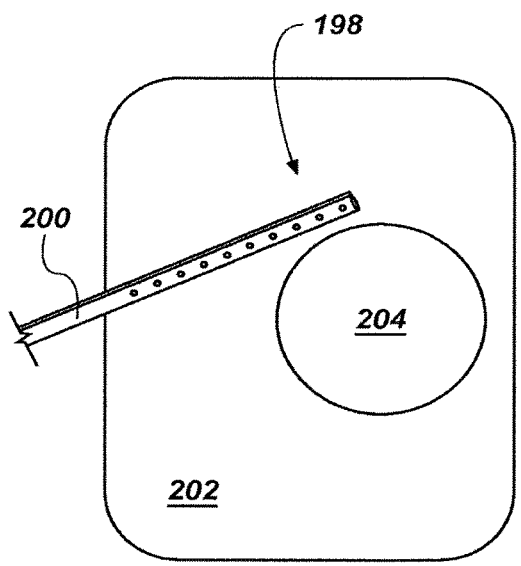
FIG. 33 shows a schematic detail view of the drainage tube of FIG. 32, wherein the distal end has been moved to a second position within the pleural cavity.
Figure 34:
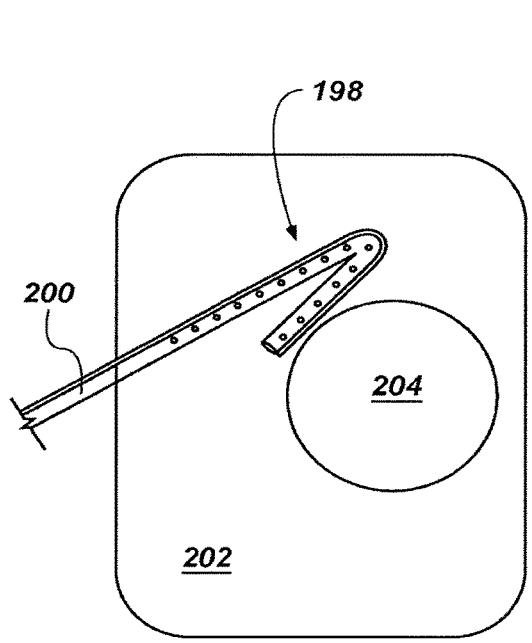
FIG. 34 shows a schematic detail view of a drainage tube having a distal end in a first position within a pleural cavity.
Figure 35:
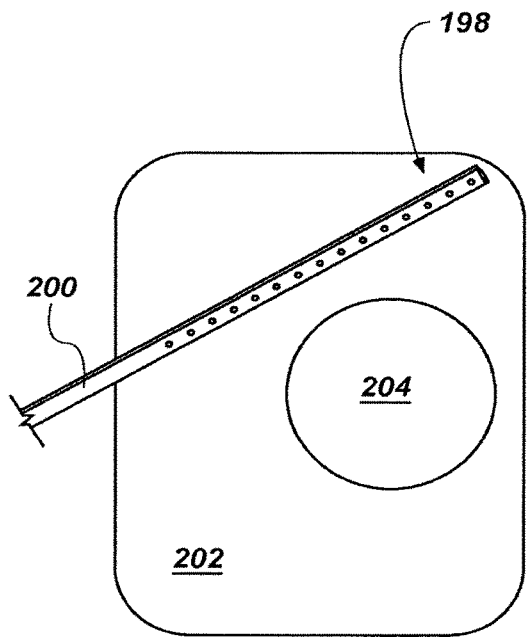
FIG. 35 shows a schematic detail view of the drainage tube of FIG. 34, wherein the distal end has been moved to a second position within the pleural cavity.
Figure 36:
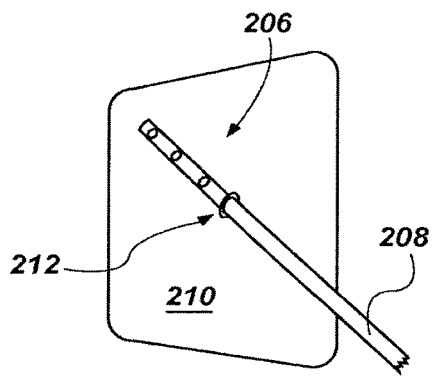
FIGS. 36 through 41 show schematic detail views of a drainage tube according to an embodiment of the present invention having a distal end positioned at different locations within a pleural cavity as a result of a movement of the distal end within the pleural cavity.
Figure 39:
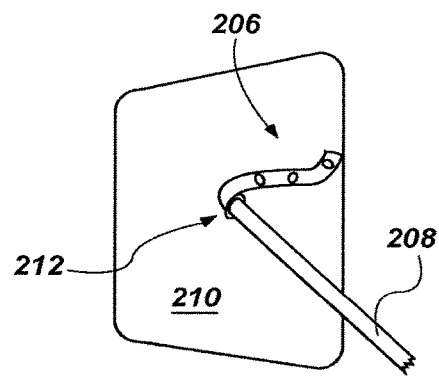
Figure 37:
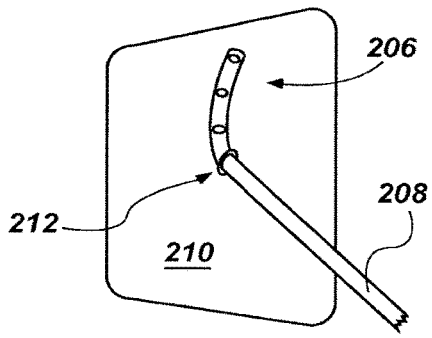
Figure 40:
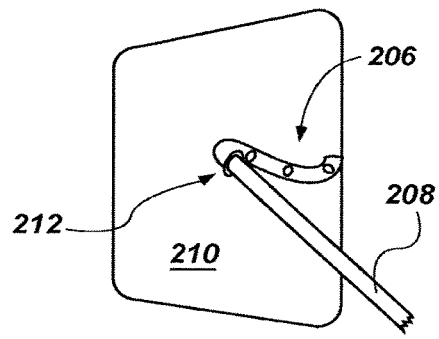
Figure 38:
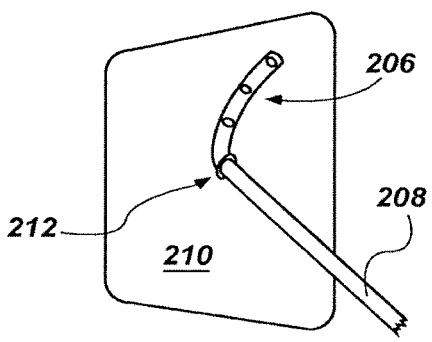
Figure 41:
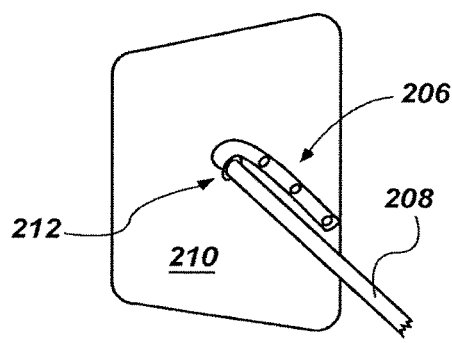

In some embodiments, a drainage tube 188 may include a plurality of open lumens 190, 192, such as shown in FIG. 31. In such embodiments, each open lumen 190; 192 may extend along a length of the drainage tube 188 and have at least one opening 194, 196 at a distal end thereof. A first open lumen 190 may have another opening at an opposing, proximal end that may be coupled to a suction source (not shown). A second lumen 192 may also have an opening at an opposing, proximal end (not shown). However, the opening at the proximal end of the second lumen 192 may be coupled to a fluid source, rather than a suction source. In view of this, a fluid may be injected into a body cavity from the fluid source through the opening 194 of the second open lumen 192 while fluid is removed from the body cavity through the openings 196 of the first open lumen 190. For example, fluids such as one or more of antibiotics, saline water, enzymes, and other fluids may be injected through the opening 194 of the second open lumen 192 into a body cavity such as for one or more of irrigation, blood thinning, medication delivery, tissue stimulation, and other treatments. Simultaneously, fluid may be removed from the body cavity through the openings 196 of the first open lumen 190.

In some embodiments, methods of utilizing a drainage tube having a moveable distal end may include determining a size and shape of a body cavity, preselecting a range of movement for a drainage tube, inserting the drainage tube into the body cavity and moving the distal end of the drainage tube within the body cavity according to the preselected range of movement. For example, body imaging technology such as X-ray imaging, ultrasound imaging, magnetic resonance imaging (MRI), and computed tomography (CT) scanning may be utilized to determine the size and shape of a body cavity. Additionally, a size and shape of a body cavity may be estimated by external measurements of a patient without utilizing body imaging technology. Next, a range of movement may be selected by utilizing the estimated size and shape of the body cavity and specific treatment objectives. For example, a range of movement about a curved surface, such as a shape of a surface of a pleural cavity defined by a chest wall, may be selected for the cleaning and drainage of the pleural cavity. After the range of movement is selected, a drainage tube may be configured to achieve the selected range of movement and may be inserted into the body cavity. After insertion into the body cavity, the distal end of the drainage tube may be moved within the body cavity according to the preselected range of movement to facilitate a specific treatment.

In view of the foregoing, embodiments may be utilized to treat and drain body cavities of patients. For example, embodiments may be utilized to move a distal end 198 of a drainage tube 200 within a pleural cavity 202, providing drainage about a lung 204, as shown in FIGS. 32 and 33 and FIGS. 34 and 35, to treat and drain an empyema or other flowable liquid, gaseous or semisolid matter from the pleural cavity 202 or from another body cavity. Embodiments that include a drainage tube having a distal end that may be moveable after insertion into a body cavity may be utilized to remove substantially all of a flowable material from a body cavity. Additionally, the moveable distal end may provide other beneficial treatments, such as the massaging of tissue, such as lung tissue. Furthermore, embodiments may provide the infusion of medication, the introduction of irrigation fluids, enzymes or other treatments into specific regions of a body cavity or may distribute such treatments over substantially all of a body cavity.

In some embodiments, a distal end 206 of a drainage tube 208 may move about a body cavity in a snake-like motion, as shown in FIGS. 36 through 41. For example, and as shown in FIGS. 36 through 41, the drainage tube 208 may be inserted at a generally central region of a pleural cavity 210 and the distal end 206 of the drainage tube 208 may move about an upper portion of the pleural cavity 210 from an insertion point 212, such as in a snake-like motion. Similarly, the drainage tube 208 may move about the lower portion of the pleural cavity 210 from the insertion point 212.

In view of the foregoing, access to various regions of a body cavity by a distal end of a drainage tube may be achieved at a single point of entry, and without requiring multiple incisions. Additionally, a drainage tube according to embodiments such as described herein may have a significantly smaller diameter than conventional drainage tubes, yet have superior efficacy. A relatively small diameter drainage tube may facilitate insertion, reduce pain and discomfort experienced by a patient, reduce bleeding, and decrease recurrent pneumothorax on withdrawal of the drainage tube. The device may be especially effective in draining or evacuating fluid from the complex configuration of a pleural cavity.

FIG. 42 shows a drainage device 214 according to another embodiment of the present disclosure. The drainage device 214 may include a drainage tube 216 configured to provide drainage to a body cavity defined by or surrounded by soft tissue. For example, the drainage device 214 may be used to withdraw infection exudates from a pleural cavity by applying suction to the drainage tube 216. In addition, positive pressure may be applied to the drainage tube 216, such as to introduce a fluid into the drainage tube 216 and/or body cavity, such as to dissolve material to be removed or to dislodge flow restrictions within the drainage tube 216. The drainage device 214 may be configured to inhibit damage to the soft tissue surrounding the cavity while a portion of the drainage device 214 is inserted into the cavity or moved about within the cavity. The drainage tube 216 may include a proximal end 218 and a distal end 220. The drainage tube 216 may include at least one of an axial opening 222 in the distal end 220 and one or more lateral openings 223 proximate the distal end 220 into an open lumen (shown in FIG. 46). The distal end 220 of the drainage device 214 may include a substantially blunted geometry to prevent damage to the body cavity, as will be explained in more detail below with reference to FIG. 46. Thus, the distal end 220 may not have any sharp, pointed, or abrupt edges that, if present, could puncture or otherwise damage soft tissue of a body cavity.

The proximal end 218 of the drainage tube 216 may be connected to an activation device 224 that may include a control device 226. The control device 226 may include, for example, a lever 228 configured to be manually manipulated by a physician or other care provider. In other embodiments, the control device 226 may be an automated actuation device that includes, for example, an electronic stepper motor, a linear actuator, a pneumatic motor or actuator, or another type of automated control system.

FIG. 43 shows a side view of the drainage device 214 of FIG. 42. The drainage device 214 may include an outlet port 230 in fluid communication with the drainage tube 216 and configured for connection to a vacuum source for removal of material from a body cavity or to a source of one or more treatments to be introduced into the body cavity. In some embodiments, the outlet port 230 may be an integral extension of the drainage tube 216.

FIG. 44 shows a cross-sectional view of the drainage device 214 of the embodiment of FIG. 42. An activation device 224 may be attached to the proximal end 218 of the drainage tube 216. The activation device 224 may include a pinion gear 232, a first rack 234, and a second rack 236. The first and second racks 234, 236 may be complementary to and meshed with the pinion gear 232. First and second flexible members 238, 240 may be attached to the first and second racks 234, 236, respectively. The first and second flexible members 238, 240 may include, for example, metallic wires made from steel, titanium, nitinol, or other metals or alloys, synthetic fibers such as nylon, polyester, or other polymers, or naturally occurring fibers such as cotton, silk, or sinew. Such wires or fibers may include a single strand or multiple strands of one or more materials bundled or woven together. For example, the first and second flexible members 238, 240 may be constructed as described above in connection with FIGS. 7-15. The first and second flexible members 238, 240 may be disposed within closed lumens within a wall (described in more detail below in connection with FIG. 46) of the drainage tube 216. The lumens through which the first and second flexible members 238, 240 extend may not be in fluid communication with the open lumen defined by the drainage tube 216 or with an exterior of the drainage tube 216. In some embodiments, the flexible members 238, 240 may be completely laterally enclosed within the walls of the drainage tube 216. The lumens may be positioned within the wall of the drainage tube 216 such that each of the flexible members 238, 240 is substantially directly opposite the other across a diameter of the drainage tube 216.

FIG. 45 shows another cross-sectional view of the drainage device 214 of the embodiment of FIG. 42. The pinion gear 232 may rotate in response to an applied torque 242. The torque 242 may be applied by the lever 228 (FIG. 42), which may be connected to the pinion gear 232, or by an automated system as described above. Rotation of the pinion gear 232 may cause generally linear movement of the first rack 234 in a first direction 244 and a corresponding movement of the second rack 236 in a second, opposite direction 246. Movement of the first rack 234 may create tension in the first flexible member 238, which imparts a compressive force to a first side 248 of the drainage tube 216. Movement of the second rack 236 may allow slack in the second flexible member 240. Such a compressive force may cause the drainage tube 216 to contract along the first side 248 in which the first flexible member 238 is disposed and lengthen along a second side 250 in which the second flexible member 240 is disposed, causing the drainage tube 216 to assume an arcuate shape, such as the shape shown in FIG. 45. The magnitude of the applied torque 242 may determine the amount of rotation of the pinion gear 232 and the corresponding amount of curvature imparted to the drainage tube 216. Torque may be applied in a direction opposite the direction indicated in FIG. 45, resulting in curvature of the drainage tube 216 in an opposite direction to the curvature shown. In some embodiments, the drainage device 214 may be configured such that the distal end 220 may rotate at least about 360° from a first fully curved position (e.g., pointing down and to the left in the perspective shown in FIG. 45) to a second, opposite fully curved position (e.g., pointing down and to the right from the same perspective).

Figure 46:
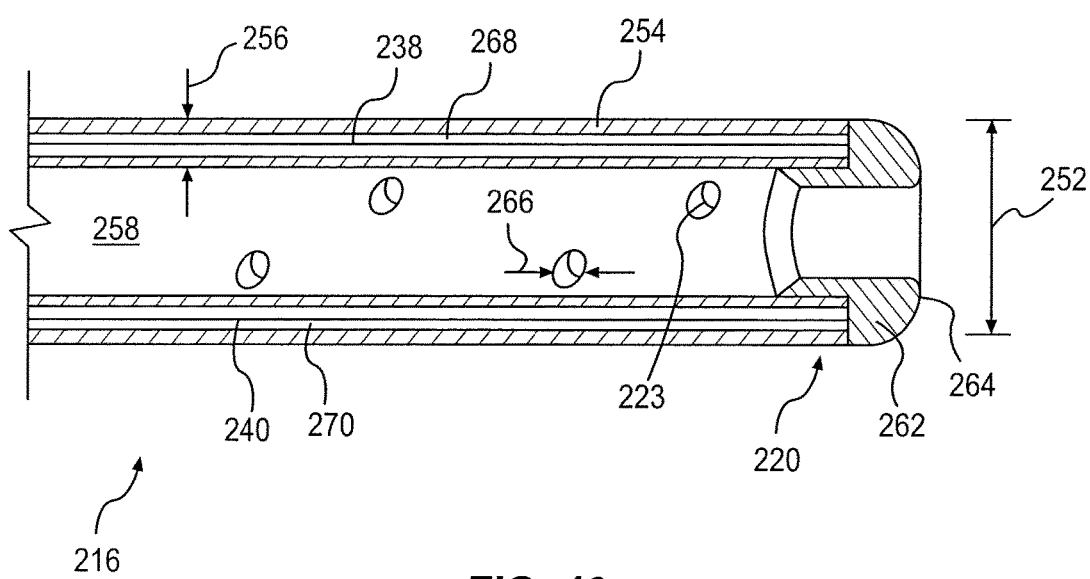
FIG. 46 shows a cross-sectional detail view of a drainage tube according to an embodiment of the present invention.

FIG. 46 shows a cross-sectional view of a portion of the drainage tube 216 proximate the distal end 220. The drainage tube 216 may include an outside diameter 252 between approximately 0.125 (⅛) inches (3.2 mm) and approximately 0.75 (¾) inches (19 mm). The drainage tube 216 may include a wall 254 with a wall thickness 256 of between approximately 0.03125 (¹⁄₃₂) inches (0.8 mm) and approximately 0.125 (⅛) inches (3.2 mm). The drainage tube 216 may be made from a polymer material, such as polyvinyl chloride (PVC), polyurethane, or silicone, for example. A material of the drainage tube 216 may be selected to exhibit a hardness that enables the desired bending of the drainage tube 216, as described above, and to facilitate the insertion of the drainage tube 216 into a body cavity without buckling. In addition, the hardness of the drainage tube 216 may be selected to inhibit collapsing of the drainage tube 216 when the drainage tube is inserted into a body cavity, particularly when suction is applied to remove material from the body cavity through the drainage tube 216. In addition, the drainage tube 216 may be configured to bend while inhibiting collapse, as explained, at a temperature of the body cavity. For example, a temperature of the body cavity may be between about 96° F. (35.6° C.) and about 105° F. (40.6° C.), which may tend to soften the material of the drainage tube compared to a relatively lower, ambient temperature. By way of example and not limitation, the material of the drainage tube 216 may exhibit a Shore A durometer measurement between approximately 75 A and approximately 95 A, such as between approximately 80 A and approximately 90 A.

The drainage tube 216 may define an open lumen 258 extending centrally through the drainage tube 216. Lateral openings 223 into the open lumen 258 may extend through the wall 254 of the drainage tube 216. The size and spacing of the lateral openings 223 may be selected to inhibit collapsing of the drainage tube 216 when the wires 238 and 240 are used to bend the drainage tube 216 and/or when a vacuum is applied to the drainage tube 216. For example, the lateral openings 223 may be spaced approximately 0.25 (¼) inch (6.4 mm) to approximately 1 inch apart and may have a diameter 266 of between approximately 0.0625 (¹⁄₁₆) inches (1.6 mm) and approximately 0.5 (½) inches (12.7 mm). In some embodiments, no two openings may be less than about 0.25 (¼) inches (6.4 mm) apart along an outer surface of the drainage tube. The openings may be arranged along a path defined by one or more substantially helical lines along an outer surface of the drainage tube 216. Such spacing may help to maintain the structural integrity and rigidity of the drainage tube and enable the drainage tube to be inserted into and used within a patient's body cavity. Furthermore, such spacing may prevent the drainage tube from collapsing under applied vacuum or under the compressive forces applied by the activation device (FIG. 45).

The drainage tube 216 may include an annular open end cap 262 with a rounded distal surface 264. Thus, at least a radially outer portion of the end cap 262 at the distal surface 264 may be curved when viewed in cross section, as shown in FIG. 46. First and second flexible members 238, 240 may be coupled to the end cap 262, such that the end cap 262 provides an anchor for the flexible members 238, 240 to enable tension to be applied to the flexible members 238, 240, as explained above. The first and second flexible members 238, 240 may be disposed within closed lumens 268 and 270 extending longitudinally through the wall 254, such that no part of the flexible members 238, 240 are exposed to the body cavity or to the open lumen 258.

The drainage tube 216 may be configured to provide both a desired range of motion through bending thereof and to resist collapsing during use within a body cavity. The range of motion and the resistance to collapse may be accomplished by balancing the outside diameter 252, the wall thickness 256, the durometer, size of the lateral openings 223, and the spacing of the lateral openings 223. As noted above, the drainage tube 216 may be configured to remove infection exudates or other materials from a body cavity, such as a pleural cavity, that is defined by relatively soft tissue. Infection exudates or other materials to be removed from a body cavity by the drainage tube 216 may be relatively viscous, such as more viscous than water or blood. To remove the viscous material from the body cavity, a relatively high suction level may be applied to the drainage tube 216, and the drainage tube 216 may have an inner diameter sufficiently large to enable and facilitate flow of the viscous material therethrough. However, the relatively high suction level and the size of the inner diameter may tend to facilitate collapse of the drainage tube 216 and resist bending and movement of the drainage tube 216 using the mechanism described above. Accordingly, the durometer of the material of the drainage tube 216, the wall thickness 256, and the size and spacing of the lateral openings 223 may be selected to inhibit such collapse while enabling the desired movement and bending. Thus, selecting the parameters of the outside diameter 252, the wall thickness 256, the durometer, the size of the lateral openings 223, and the spacing of the lateral openings 223 to fall within the ranges listed above may enable the drainage tube 216 to be moved (e.g., bent) a desired distance within the body cavity, while enabling a sufficient suction to be applied for removing material from a body cavity, as desired, without collapsing.

The drainage device may be configured to be inserted into a body cavity of a patient and remain inside the cavity for extended periods of time such as hours, days, weeks, or even months. A physician or other care provider may operate the manual or automatic activation device to cause the distal end of the drainage device to move within the body cavity, such as to reach fluid or other material that is to be removed from the body cavity. Such movement may be continuous or periodic. In some embodiments, an automatic activation device such as described in connection with FIG. 42 may be connected to a timer that initiates periodic movement while the drainage device is in the body cavity, such as at a predetermined number of minutes, hours, or days.

Accordingly, embodiments of drainage devices the present disclosure may be suitable for removing material from body cavities that are defined by soft tissues and for being moved within such body cavities without repositioning a base or proximal end thereof. In contrast, other prior known tubular devices for insertion into bodies may not be suitable for removing material from soft body cavities while being capable of bending and movement within the body cavities with a range of movement comparable to the drainage tube of the present disclosure. For example, tubular devices for sampling bone marrow may be formed of a material having a sufficiently high durometer and/or wall thickness to avoid collapse under suction, but such devices may not exhibit the same range of movement when bent or moved. In addition, the harder materials of such devices may exhibit a higher likelihood of damaging soft tissues, which is not a concern for devices that are configured to be inserted into cavities surrounded by bone. By way of another example, tubular devices with cameras thereon for exploring body cavities may be sufficiently soft to inhibit damaging soft tissues and to move or bend within the body cavities, but collapse of such tubular devices is generally not an issue since suction is not applied thereto and material is not removed by such devices. In addition, prior known tubular devices that are used to remove material from soft body cavities by suction are not configured to move or bend in the manner described in the present disclosure, and are often required to be repositioned by forming multiple incisions. Accordingly, the drainage devices of the present disclosure may exhibit advantages over prior known tubular devices for at least certain applications.

While the invention may be susceptible to various modifications and alternative forms, specific embodiments have been shown by way of example in the drawings and have been described in detail herein. However, it should be understood that the invention is not intended to be limited to the particular forms disclosed. Additionally, embodiments and features of the invention shown and/or described separately may be combined.

What is claimed is:

1. A body cavity drainage device for a patient, comprising:
   a drainage tube having a proximal end, a distal end, and a wall, the distal end being configured to be inserted into a body cavity of the patient defined by soft tissue during use of the body cavity drainage device, the drainage tube defining an open lumen extending centrally therethrough, the drainage tube comprising:
      a plurality of openings extending through a sidewall of the drainage tube proximate the distal end and providing fluid communication between a body cavity of the patient and the open lumen; and
   an activation device attached to the proximal end of the drainage tube and configured to be positioned at least partially external to the patient during use of the body cavity drainage device, the activation device operably connected to the first and second flexible members and configured to apply a tension to the first and second flexible members to bend the drainage tube, wherein the activation device comprises:
      an outlet port in fluid communication with the open lumen of the drainage tube;
      a control device comprising a lever configured to be manually manipulated by a user;
      a pinion gear rigidly attached to the control device such that the pinion gear and the control device have a common axis of rotation;
      a first rack meshed with the pinion gear;
      a second rack meshed with the pinion gear; and
      first and second flexible members extending along a length of the drainage tube and attached to the drainage tube at or near the distal end of the drainage tube, each of the first and second flexible members attached to the first and second racks, respectively, wherein the first and second flexible members are woven from an outside surface of the drainage tube through the plurality of openings extending through the sidewall of the drainage tube into the open lumen as the first and second flexible members extend from the first and second racks to the distal end of the drainage tube.

2. The body cavity drainage device of claim 1, wherein the drainage tube comprises a polyvinyl chloride material, a polyurethane material, or a silicone material.

3. The body cavity drainage device of claim 1, wherein the drainage tube comprises a material exhibiting a Shore A durometer measurement of between about 75 A and about 95 A.

4. The body cavity drainage device of claim 1, wherein the distal end of the drainage tube comprises a radially outer surface that is curved when viewed in cross section.

5. The body cavity drainage device of claim 4, wherein each opening of the plurality of openings comprises a diameter between about 0.125 inch and about 0.375 inch.

6. The body cavity drainage device of claim 1, wherein each opening of the plurality of openings into the open lumen is spaced along one or more helical paths extending along at least a portion of a length of the drainage tube.

7. A body cavity drainage device for a patient, comprising:
   a drainage tube having a proximal end and a distal end and defining an open lumen extending centrally therethrough, the drainage tube comprising:
      an activation device disposed at the proximal end of the drainage tube, the activation device comprising:
         an outlet port in fluid communication with the drainage tube;
         a control device comprising a lever configured to be manually manipulated by a user;
         a pinion gear rigidly attached to the control device such that the pinion gear and the control device have a common axis of rotation;
         a first rack meshed with the pinion gear;
         a second rack meshed with the pinion gear; and
         first and second flexible members extending along a length of the drainage tube and attached to the drainage tube at or near the distal end of the drainage tube, each of the first and second flexible members attached to the first and second racks, respectively, wherein the first and second flexible members are woven from an outside surface of the drainage tube through the plurality of openings extending through the sidewall of the drainage tube into the open lumen as the first and second flexible members extend from the first and second racks to the distal end of the drainage tube.

8. The body cavity drainage device of claim 7, wherein the distal end of the drainage tube comprises laterally extending protrusions for massaging internal body tissue.

9. A body cavity drainage device for a patient, comprising:
   a drainage tube having a proximal end and a distal end and defining an open lumen extending centrally therethrough, the drainage tube comprising:
      a plurality of openings extending through a sidewall of the drainage tube proximate the distal end and providing fluid communication between a body cavity of the patient and the open lumen; and
   an activation device disposed at the proximal end of the drainage tube, the activation device comprising:
      an outlet port in fluid communication with the open lumen of the drainage tube;
      a pinion gear attached to an automated control device, wherein the automated control device comprises at least one of a linear actuator, a magnetic field generating device, or an electronic stepper motor;
      a first rack meshed with the pinion gear;
      a second rack meshed with the pinion gear; and
      first and second flexible members extending along a length of the drainage tube and attached to the drainage tube at or near the distal end of the drainage tube, each of the first and second flexible members attached to the first and second racks, respectively, wherein the first and second flexible members are woven from an outside surface of the drainage tube through the plurality of openings extending through the sidewall of the drainage tube into the open lumen as the first and second flexible members extend from the first and second racks to the distal end of the drainage tube.

10. The body cavity drainage device of claim 9, wherein the distal end of the drainage tube comprises laterally extending protrusions for massaging internal body tissue.

11. The body cavity drainage device of claim 9, wherein the first and second flexible members comprise metallic wires, the metallic wires comprising at least one of steel, titanium, or nitinol.

12. The body cavity drainage device of claim 9, wherein the first and second flexible members comprise fibrous material, the fibrous material comprising at least one of nylon, polyester, cotton, silk, or sinew.

13. The body cavity drainage device of claim 7, wherein the outlet port is configured for connection to a vacuum source for removal of material from a body cavity of the patient.

14. The body cavity drainage device of claim 9, wherein the first and second flexible members are laterally enclosed within a wall of the drainage tube.

15. The body cavity drainage device of claim 7, wherein the distal end of the drainage tube is configured to rotate at least about 360 degrees from a first curved position to a second, opposite curved position.

16. The body cavity drainage device of claim 7, wherein the outlet port comprises an integral extension of the drainage tube.

17. The body cavity drainage device of claim 9, wherein the outlet port comprises an integral extension of the drainage tube.

18. The body cavity drainage device of claim 7, wherein the drainage tube further comprises an axial opening in the distal end of the drainage tube.

19. The body cavity drainage device of claim 9, wherein the drainage tube further comprises an axial opening in the distal end of the drainage tube.

20. The body cavity drainage device of claim 7, wherein each of the first and second racks has an arcuate shape.

* * * * *